(12) United States Patent
Wang et al.

(10) Patent No.: US 12,133,896 B2
(45) Date of Patent: Nov. 5, 2024

(54) METHODS FOR TREATING OR ALLEVIATING A BONE-LOSS RELATED DISEASE OR CONDITION BY ADMINISTERING A NUCLEIC ACID ENCODING A DISCOIDIN DOMAIN RECEPTOR 1 (DDR1) PROTEIN

(71) Applicant: Kaohsiung Medical University, Kaohsiung (TW)

(72) Inventors: Chau-Zen Wang, Kaohsiung (TW); Chung-Hwan Chen, Kaohsiung (TW); Liang-Yin Chou, Kaohsiung (TW); Yu Chou, Kaohsiung (TW); Mei-Ling Ho, Kaohsiung (TW); Yi-Hsiung Lin, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 945 days.

(21) Appl. No.: 17/168,873

(22) Filed: Feb. 5, 2021

(65) Prior Publication Data
US 2021/0162074 A1 Jun. 3, 2021

Related U.S. Application Data

(63) Continuation-in-part of application No. 16/496,666, filed as application No. PCT/CN2018/080238 on Apr. 24, 2018, now Pat. No. 10,946,021.

(60) Provisional application No. 62/475,397, filed on Mar. 23, 2017.

(51) Int. Cl.
| | | |
|---|---|---|
| A61K 48/00 | (2006.01) | |
| A61K 9/00 | (2006.01) | |
| A61K 9/127 | (2006.01) | |
| A61K 35/76 | (2015.01) | |
| A61K 38/45 | (2006.01) | |
| A61P 19/00 | (2006.01) | |
| A61P 19/10 | (2006.01) | |
| C12N 7/00 | (2006.01) | |
| C12N 15/86 | (2006.01) | |

(52) U.S. Cl.
CPC ........ *A61K 48/0058* (2013.01); *A61K 9/0019* (2013.01); *A61K 9/127* (2013.01); *A61K 38/45* (2013.01); *A61K 48/0075* (2013.01); *A61P 19/00* (2018.01); *A61P 19/10* (2018.01); *C12N 7/00* (2013.01); *C12N 15/86* (2013.01); *A61K 35/76* (2013.01); *C12N 2740/15043* (2013.01)

(58) Field of Classification Search
CPC .. A61K 48/0058; A61K 9/0019; A61K 9/127; A61K 38/45; A61K 48/0075; A61K 35/76; C12N 7/00; C12N 15/86; C12N 2740/15043
See application file for complete search history.

(56) References Cited

U.S. PATENT DOCUMENTS

| | | |
|---|---|---|
| 9,732,215 B2 | 8/2017 | Adamkewicz |
| 10,370,360 B2 | 8/2019 | Brekken |

FOREIGN PATENT DOCUMENTS

| | | |
|---|---|---|
| CN | 103965195 A | 8/2014 |
| KR | 20100060300 A | 6/2010 |
| WO | 2008021369 A2 | 2/2008 |
| WO | 2008058341 A1 | 5/2008 |
| WO | 2010062038 A2 | 6/2010 |
| WO | 2013068836 A1 | 12/2012 |
| WO | 2013074986 A1 | 5/2013 |
| WO | 2016064970 A1 | 4/2016 |

OTHER PUBLICATIONS

Borza et al., 2014, Discoidin domain receptors in disease, Matrix biology, 34, 185-192.
Gao et al., 2013, Discovery and optimization of 3-(2-)pyrazolo[1,5-a]pyrimidin-6-yl)-ethynyl)benzamides as novel selective andorally bioavailable discoidin domain receptor 1 (DDR1) inhibitors, J of Med Chem, 56, 3281-3295.
Wang et al., 2012, BMP-2 collagen sponge repair the rabbit ear cartilage defects in rabbits, National Medical Frontiers of China, vol. 2, No. 2, 31 (Abstract in English).
Chou et al. 2020 Discoiding Domain Receptor 1 Regulates Runx2 during Osteogenesis of Osteoblasts and Promotes Bone Ossification via Phosphorylation of p38, International Journal of Molecular Sciences, 21, 7210; doi: 10.3390/jms21197210.
International Search Report and English translation issued for PCT/CN2018/080238 dated Apr. 25, 2018.
Written Opinion issued for PCT/CN2018/080238 dated Apr. 25, 2018.
Office Action issued for Taiwanese Application No. TW107109902 dated Apr. 30, 2019.

*Primary Examiner* — Robert S Landsman
(74) *Attorney, Agent, or Firm* — Volpe Koenig

(57) ABSTRACT

The present invention relates to a method for treating or alleviating an osteoporosis in a subject. The method comprises steps of identifying the subject having the osteoporosis, and administering to the subject an effective amount of a composition that increases a level of Discoidin Domain Receptor 1 (DDR1) protein in the subject.

16 Claims, 25 Drawing Sheets
(12 of 25 Drawing Sheet(s) Filed in Color)

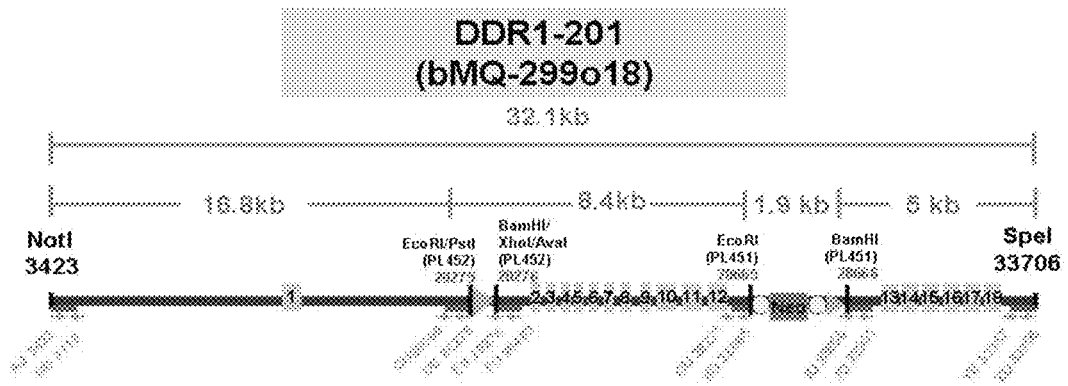
Fig. 1A
Fig. 1B
Fig. 1C
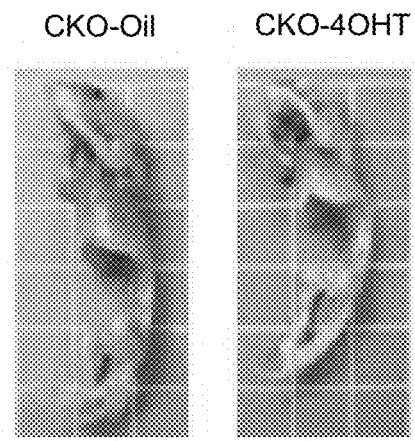
Fig. 1D

FF-4OHT

CKO-4OHT

METHODS FOR TREATING OR ALLEVIATING A BONE-LOSS RELATED DISEASE OR CONDITION BY ADMINISTERING A NUCLEIC ACID ENCODING A DISCOIDIN DOMAIN RECEPTOR 1 (DDR1) PROTEIN

CROSS-REFERENCE TO RELATED APPLICATION AND CLAIM OF PRIORITY

This application is a Continuation-In-Part of application Ser. No. 16/496,666 (now U.S. Pat. No. 10,946,021) filed on Sep. 23, 2019, and for which priority is claimed under 35 U.S.C. § 120; and this application claims the benefit of the U.S. Patent Application No. 62/475,397, filed on Mar. 23, 2017 and the PCT Patent Application No. PCT/CN2018/080238, filed on Apr. 24, 2018; the entire contents of all are hereby incorporated by reference.

FIELD OF THE INVENTION

The present invention is related to methods and compositions for treating or alleviating bone-loss related diseases, in particular to diseases related to osteoporosis.

BACKGROUND OF THE INVENTION

Discoidin domain receptors (DDRs) including DDR1 and DDR2 are members of receptor tyrosine kinases (RTKs) that may be stimulated by collagens. Unlike other RTKs, DDRs contain two discoidin domains in the extracellular region. DDRs are activated by a number of triple-helical collagens, which are the most abundant components of the extracellular matrix (ECM). DDR1 is widely expressed in epithelial cells in the lung, kidney, colon and brain, whereas DDR2 is primarily expressed in mesenchymal cells including fibroblasts, myofibroblasts, smooth muscle, and skeletal cells in kidney, skin, lung, heart, and connective tissues. Studies demonstrated that both DDR1 and DDR2 play crucial roles in fundamental cellular processes, such as proliferation, survival, differentiation, adhesion, and matrix remodeling. Deregulation of DDR1 and DDR2 has been shown to be implicated in a number of diseases, including fibrotic disorders, atherosclerosis, and cancer. Although DDR1 and DDR2 belong to the same family, DDR1 and DDR2 are two different functional proteins, and the ligands responsible for activating DDR1 and DDR2 are also different. DDR1 can be activated by all types of collagens, including collagen types I to IV and collagen type VIII, whereas DDR2 can only be activated by collagen types I, III, and X. The function, use and involved signal pathway of DDR1 cannot be regarded as equivalent to those of DDR2.

DDR1 is currently known to play an important role in bone development, but the relevant mechanisms of DDR1 in bone development and cartilage development remain unclear. In a normal adult, both bone resorption and bone formation are strictly controlled, so there is only a little change in total bone mass. However, if a patient suffering from diseases associated with decrease in bone mass, balance between bone resorption and bone formation is lost and the decreased bone mass and deterioration of bone tissue occur.

A representative disease associated with decrease in bone mass includes osteoporosis. Osteoporosis, characterized by bone loss and high risk of fractures, is one of the commonest diseases particularly in old age and postmenopausal woman, and is estimated to affect approximately 100 million people worldwide. While the incidence of bone fracture in the elderly is generally increasing, therapeutic choices are limited. Currently, antiresorptives (e.g. bisphosphonates, denosumab, hormone therapy) are the most commonly used treatments for osteoporosis. These agents are designed to slow bone remodeling and increase bone density. However, they have been associated with significant side effects including osteonecrosis of the jaw, atypical fractures, atrial fibrillation, and increased risk of stroke or cancer. Anabolic agents may be used to generate new bone in patients with osteoporosis. However, finding anabolic factors that increase bone mass and regulate the balance between osteoblast-mediated bone formation and bone marrow adiposity has been challenging. In addition, the commercially available anabolic agent (teriparatide, which is a form of parathyroid hormone) is not only very expensive and difficult to administer but is also associated with side effects including lowered blood pressure, nausea, pain, weakness, and depression. Moreover, the use of teriparatide in rats has been found to cause malignant tumor growth (osteogenic carcinoma). Estrogen replacement therapy (ERT) is a fairly common treatment to conserve bone mass and prevent osteoporosis-related fractures in post-menopausal women, but the therapy has been connected to increased risks of uterine cancer, breast cancer, stroke, heart attacks, blood clots, and even mental decline. In general, therapeutic choices for osteoporosis are limited and the development of new therapeutic approaches that stimulate bone formation is preferred.

Therefore, what is needed in the art is a new composition or method for treating or alleviating bone loss related diseases, particularly osteoporosis, and promoting bone growth.

In view of the above, because of the defect in the prior art, the inventors have provided the present invention to effectively overcome the demerits in the prior art. The descriptions of the present invention are as follows:

SUMMARY OF EXEMPLARY EMBODIMENTS

The present invention provides compositions and methods useful for, but not limited to, treatment and/or alleviation of bone-loss related diseases or symptoms for the loss of bone density, mass, or mineral content with the additional benefit of avoiding the harmful side effects, such as an increased risk of cancer, that may caused by hormone drugs. The present invention also provides compositions and methods useful for change of bone architecture and bone biomechanical strength. The present invention also discloses a use of compostions that increase a level of Discoidin Domain Receptor 1 (DDR1) protein in effectively relieving and treating bone-loss related diseases by increasing the DDR1 level in a subject.

One object of this application is to provide a method for treating or alleviating an osteoporosis in a subject. The method comprises steps of identifying the subject having the osteoporosis, and administering to the subject an effective amount of a composition that increases a level of Discoidin Domain Receptor 1 (DDR1) protein in the subject.

Another object of this application is to provide a method for treating or alleviating a bone-loss related disease or condition in a subject. The method comprises a step of administering to the subject an effective amount of a composition that increases a level of Discoidin Domain Receptor 1 (DDR1) protein in the subject for treating or alleviating the bone-loss related disease or condition in the subject.

Another object of this application is to provide a pharmaceutical composition for treating or alleviating a bone-loss related disease or condition in a subject. The pharmaceutical composition comprises a gene therapy vector. The gene therapy vector comprises a nucleic acid sequence connected with an osteoblast specific promoter and encoding a Discoidin Domain Receptor 1 (DDR1) protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above embodiments and advantages of the present invention will become more readily apparent to those ordinarily skilled in the art after reviewing the following detailed descriptions and accompanying drawings:

FIG. 1A shows the synthetic vector for the chondroblast-specific transgenic mice (a1(II)-Cre/Ddr1$^{flox/flox}$ mice).

FIG. 1B shows the DNA electrophoretic pattern of the chondroblast-specific transgenic mice (a1(II)-Cre/Ddr1$^{flox/flox}$ mice) for identifying DDR1$^{flox/flox}$.

FIG. 1C shows the DNA electrophoretic pattern of the chondroblast-specific transgenic mice (a1(II)-Cre/Ddr1$^{flox/flox}$ mice) for identifying Co1(II)-Cre/ERT.

FIG. 1D shows that the transgenic mice with specific deletion of DDR1 in chondroblasts (i.e., CKO mice injected with 4OHT, indicated by "CKO-4OHT") have smaller bodies compared to the control group (i.e., CKO mice injected with oil, indicated by "CKO-Oil").

In FIG. 6B, the upper two small figures have a magnification of 100 times and a scale bar of 200 μm, and the lower six small figures have a magnification of 400× and a scale bar of 50 μm.

DETAILED DESCRIPTION OF THE PREFERRED EMBODIMENTS

Figure 1E:
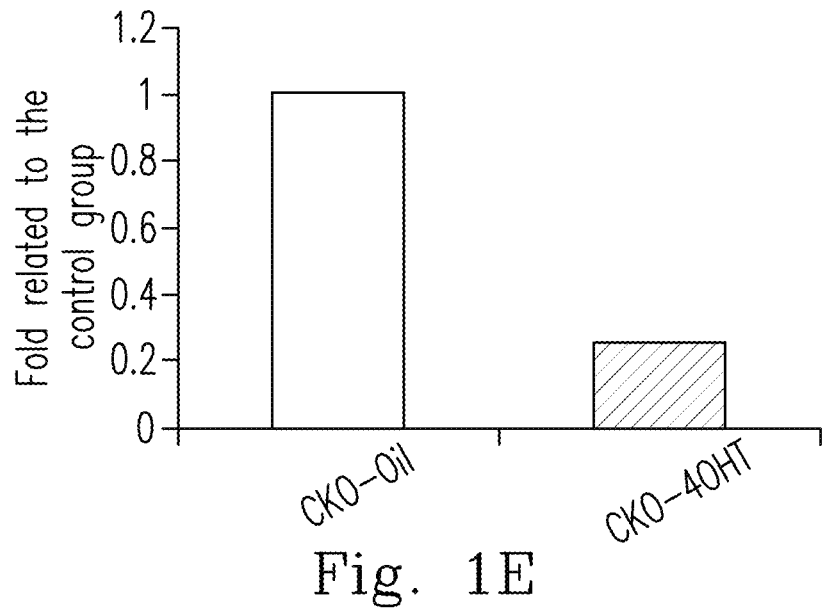
FIG. 1E shows that when compared to the control group (CKO-Oil), the DDR-1 protein level was significantly inhibited in the CKO-4OHT mice, which was shown by the western blot method and the corresponding statistical graph.

The invention provided in the present application will be fully understood by the following embodiments, so that those having ordinary knowledge in the art can achieve the invention. However, the implementation of the present invention is not limited by the following embodiments, and other embodiments can be deduced according to the spirit of the disclosed embodiments. These embodiments all fall into the scope of the present invention.

Definitions

Unless otherwise limited in the specific examples, the following definitions can be applied to the terms used throughout the specification.

The term "pharmaceutically acceptable salts" means salts of the compounds having the pharmacological activity of the parent compound.

The term "treatment" for any disease or disorder means complete or partial alleviation or retard of the occurrence of the disease or the disorder or its signs or symptoms; and/or partial or complete cure or alleviation of the disease or the disorder and/or the adverse effects caused by the disorder.

The term "therapeutically effective amount" means an amount of a compound sufficient to effect treatment of a disease when the compound is administered to a patient to treat the disease. The term "therapeutically effective amount" will vary depending on the compound, the regime of administration, the disease and its severity, and the age, weight, etc. of the patient to be treated.

The term "CKO mice" means DDR1-null mice (a1(II)-Cre/Ddr1$^{flox/flox}$ mice) in which the DDR1 gene in chondroblasts is specifically knocked out. The CKO mice were obtained by crossing the offspring of a1(II)-Cre/Ddr1$^{flox/+}$ mice, which were obtained by crossing Ddr1$^{flox/flox}$ transgenic mice with a1(II)-collagen-Cre transgenic mice. In other words, the CKO mice are like mice with a knockout switch, wherein the switch can be turned on to delete DDR1 by giving 4-OHT, and thus the DDR1 gene in chondroblasts can be specifically knocked out (wherein the CKO mice with the DDR1 knocked out are referred to as "CKO-4OHT mice" or "CKO-4OHT"). In the CKO mice given oil as a placebo (hereinafter referred to as "CKO-Oil mice" or "CKO-Oil"), the switch to knock out DDR1 is unable to be turned on.

The term "OKO mice" means DDR1-null mice (a1(I)-CreERT/Ddr1$^{flox/flox}$ mice) in which the DDR1 gene in osteoblasts is specifically knocked out. The OKO mice were obtained by crossing a1(I)-CreERT and Ddr1$^{flox/flox}$ transgenic mice. In other words, the OKO mice are like mice with a knockout switch, wherein the switch can be turned on to delete DDR1 by giving 4-OHT, and thus the DDR1 gene in osteoblasts can be specifically knocked out. The OKO mice with the DDR1 knocked out are referred to as "OKOΔDdr1 mice", "OKOΔDdr1", "OKO-4OHT" or "OKO-4OHT mice"), wherein in "OKOΔDdr1 (mice)", DDR1 in osteoblasts is knocked out by 4-OHT intraperitoneal injected 4 mg/kg in premature mice, and in "OKO-4OHT (mice)", DDR1 in osteoblasts is knocked out by 4-OHT intraperitoneal injected 4 mg/kg in mice.

The term "Ddr1$^{f/f-4OHT}$" or "FF-4OHT" as used herein refer to Ddr1$^{flox/flox}$ transgenic mice intraperitoneally injected with 4-OHT, and is used as a control group in the experiments.

The term "bone-loss related disease" as used herein refers to a disease or condition associated with abnormality of the bone that can be treated by increasing bone mass and/or bone growth. For instance, the bone disease or condition may include: primary osteoporosis; secondary osteoporosis; osteogenesis imperfecta; osteodystrophy; osteopenia; Paget's disease; osteolytic lesions produced by bone metastasis, radiotherapy, or chemotherapy; periodontal disease; alveolar bone loss; bone loss due to sex hormone deficiency; bone loss due to metastatic cancer; bone and cartilage loss caused by an inflammatory disease; osteotomy bone loss; childhood idiopathic bone loss; curvature of the spine; and bone fractures.

The term "subject" as used herein refers to a mammal, preferably a human. For instance, these subjects may include subjects who are i) older persons (male or female); and ii) females with decreased ovarian function or failure thereof.

The term "gene therapy" includes "ex vivo gene therapy" and "in vivo gene therapy". The term "ex vivo gene therapy" refers to methods where patient cells are genetically modified outside the subject, for example to express a therapeutic gene. Cells with the new genetic information are then returned to the subject from whom they were derived. The term "in vivo gene therapy" refers to methods where a vector carrying the therapeutic gene(s) is directly administered to the subject.

As used herein "vector", or "gene therapy vector", used interchangeably herein, refers to gene therapy delivery vehicles, or carriers, that deliver therapeutic genes to cells. A gene therapy vector is any vector suitable for use in gene therapy, e.g., any vector suitable for the therapeutic delivery of nucleic acid polymers (encoding a polypeptide or a variant thereof) into target cells of a patient. In some embodiments, the gene therapy vector delivers the nucleic acid encoding a therapeutic protein or therapeutic fusion protein to a cell where the therapeutic protein or fusion is expressed and secreted from the cell. The vector may be of any type, for example it may be a plasmid vector or a minicircle DNA. Typically, the vector may be a viral vector or a nonviral vector such as liposomes. The viral vector may for example be derived from an adeno-associated virus (AAV), a retrovirus, a lentivirus, a herpes simplex virus, or an adenovirus.

Biological Experiments

Transgenic Mice (a1(II)-Cre/Ddr1$^{flox/flox}$ Mice; CKO Mice)

To avoid the interference limitation of the systemic Ddr1 knockout mouse, the inventors pioneered the conditional knockout of the DDR1$^{flox/flox}$ transgenic mice model using the Cre-LoxP system based on the Cre recombinase and the loxP sequences. As shown in FIG. 1A, loxP was ligated at both ends of exon 2 and exon 12 of the DDR1 locus. The targeting vector (P1253) harboring floxed Ddr1 site and the neomycin resistance (NeoR) cassette were electroporated into embryonic stein (ES) cells derived from 129P2 background mice. The ES cells containing the floxed Ddr1 allele were injected into blastocysts of C57BL/6 embryos to generate chimeric mice, and the offspring were crossed with flippase (FLP) transgenic mice to remove NeoR franked by the FLP recombinase targete (FRT) sequence. The hybrid mice were backcrossed with C57BL/6 strain (C) for 12 generations to produce Ddr1$^{flox/flox}$ mice, which were further maintained on a C57BL/6J genetic background. A1(II)collagen-Cre/-Ddr1$^{flox/flox}$ mice are chondrocytes-specific Ddr1-deficient mice. A1(II)-Cre/Ddr1$^{flox/flox}$ mice (hereinafter referred to as CKO mice), which are chondroblast-specific DDR1 knockout mice, were obtained by intercrossing the offspring of a1(II)-Cre/Ddr1$^{flox/+}$ mice, which were obtained by crossing Ddr1$^{flox/flox}$ transgenic mice with a1(II)-collagen-Cre transgenic mice (referring to FIG. 1B to FIG. 1C). Genotyping was performed via polymerase chain reaction (PCR) using tail genomic DNA. The presence of the 3'loxP site was verified by PCR using primers.

For Cre-LoxP system, the targeted integration (knockin) of loxP sites via homologous recombination (HR) and the expression of inducible Cre recombinase is required. The ligand binding domain of the estrogen receptor (ER) was fused with Cre recombinase to form a fusion protein (Cre-ER) localized in the cytoplasm. In this way, the time-specific regulation of gene recombination can be achieved by controlling the injection time of estrogen. In order to avoid interference with endogenous estrogen, a point mutation (G521R) in the ligand binding domain of human ER allows Cre-ER to respond only to the induction of exogenous synthetic estrogen (e.g., 4-hydroxytamoxifen, 4-OHT), and such Cre-ER is named as Cre-ERT. Another fusion protein (Cre-ERT2) of Cre and a mutated ligand binding domain (LBD) of human estrogen receptor ERT2 was shown to have a much higher sensitivity to 4-OHT than Cre-ERT. Cre-ERT2 has three point mutations in human ER LBD: C400V/M543A/L544A. If Cre-ERT2 is designed to locate after a tissue-specific promoter and the resultant mice are crossed with flox mice, a spatio-temporal specific knockout of a target gene can be achieved by administering 4-OHT at a specific time point. That is, a fusion protein of Cre and a mutated ligand binding domain of human estrogen receptor ERT2 is commonly used to control Cre activity by 4-OHT, which promotes CreERT2 translocation from the cytoplasm to the nucleus where the Cre recognizes and recombines loxP sites embedded in the genomic DNA. In short, 4-OHT acts like a switch that can initiate gene knockout. During the embryonic period, 4-OHT-injected mice will initiate gene knockout, and for mice without 4-OHT (i.e., mice injected with olive oil during embryonic period as the control group), no gene knockout occurred. The 4-OHT controlled gene knockout is used in the present application to assess the immediate impact of DDR1 gene loss.

Transgenic Mice (a1(I) Collagen-CreERT/Ddr1$^{flox/flox}$ Mice; OKO Mice)

Ddr1$^{flox/flox}$ transgenic mice were obtained as previously described. The inducible a1(I)-collagen-CreERT [B6.Cg.Tg (Col1a1-Cre/ERT2)1Crm/J] cassette contains a 2.3 kb fragment of the Col1a1 promoter, Cre recombinase, ERT2, and polyA and was purchased from Jackson Laboratories. Next, a1(I)-CreERT and Ddr1$^{f/f-4OHT}$ mice were crossed to generate a1(I)-collagen-CreERT/Ddr1$^{flox/flox}$ mice (hereinafter referred to as OKO mice), which are osteoblast-specific Ddr1-deficient mice. Genomic DNA from tail tips was extracted, and gene expression was confirmed by polymerase chain reaction (PCR). The presence of the 3' loxP and Cre sites was verified by PCR.

Part I. Basic Study for CKO-Oil Mice and CKO-4OHT Mice.

1. Materials and Methods

CKO-Oil Mice and CKO-4OHT Mice 50 mg of 4-OHT powders (T5648, Sigma-Aldrich, St, Louis, MO, USA) were dissolved in 50 μl of DMSO and shaken overnight to prepare a stock solution. The stock solution was dissolved in a mixed solution of corn oil (C8267, Sigma-Aldrich) and DMSO of 9:1 for a working concentration of 4 mg/day/kg of mouse weight. On the 21$^{st}$ day of pregnancy, 4-OHT (4 mg/day/kg of mouse weight) and progesterone (P0130, Sigma-Aldrich, 2 mg/day/kg of mouse weight) or olive oil were intraperitoneally (IP) injected into embryos of the mother mice. After the mice were born, 4-OHT (4 mg/day/kg mouse weight) or oil was intraperitoneally injected daily to the mice for one week to obtain 1-week-old CKO-4OHT mice injected with 4-OHT and the CKO-Oil mice injected with oil. Alternatively, after the mice were born, the mice were intraperitoneally injected with 4-OHT (4 mg/day/kg mouse weight) or oil for 5 consecutive days and then rested for 2 days for two or four cycles to obtain 2-week-old and 4-week-old CKO-4OHT mice injected with 4-OHT and 2-week-old and 4-week-old CKO-Oil mice injected with oil.

Immunohistochemical Staining (IHC Staining)

Immunohistochemical staining involves the process of identifying the target antigens in cells or a tissue section by exploiting the principle of antibodies being conjugated to a fluorophore or an enzyme that can catalyse a colour-producing reaction and binding specifically to antigens in biological tissues. This method can be used not only to detect the expressed amount of antigen but also to observe the position of the expressed antigen. IHC staining herein was performed by using the Impress Cruz staining system (Santa Cruz Biotechnology Inc.) as follows: The collected tibia were fixed with 10% formalin solution, decalcified with 1% formic acid solution at 4° C., embedded in paraffin, and then cut into slices having a thickness of 5 μm. Deparaffinization and rehydration were performed for the tibia slices. Antigen retrieval was performed in 2.5% of hyaluronidase (H4272, Sigma-Aldrich) and 0.1% of proteinase K (P8107S, BioLabs, New England) in 1×PBS solution for 10 min. The slices were placed in 3% hydrogen peroxide for 10 minutes at room temperature, and then cultured in IX PBS solution containing 5% bovine serum albumin (A2153, Sigma-Aldrich) at 37° C. for 1 hour to avoid non-specific binding. The primary antibody was diluted with the above solution, followed by addition of tibia slices at 4° C. overnight. The primary antibody used in this assay and its dilution ratio are as follows: anti-Ki-67 antibody, 1:250 (AB9260, Millipore); anti-Sox-9 antibody, 1:250 (AB5535, Millipore); anti-collagen type II antibody, 1:250 (ab34712, abcam); anti-collagen type X antibody, 1:250 (LB-0092, Cosmo Bio Co LTD); anti-Ddr1 antibody, 1:250 (PAS-29316, Thermo Fisher Scientific In); anti-Ihh antibody, 1:100 (TA334682, Origene); and anti-PTHrP antibody, 1:300 (ab52919, abcam). After washing with PBS, a secondary antibody diluted 1:400 was added and reacted at room temperature for 1 hour. The secondary antibody may be a peroxidase-conjugated AffiniPure Goat Anti-rabbit IgG (125510, Jackson immunoresersch) or a peroxidase-conjugated AffiniPure Goat Anti-mouse IgG (Jackson immunoresersch). The DAB substrate kit (ab64238, Abcam) was used to enhance the signal, and the slices were finally counterstained with hematoxylin and observed under a microscope.

Quantitative Real-Time PCR (RT-qPCR) Analysis

The muscles and tendons of 4 to 5 days old newborn CKO-4OHT and CKO-Oil mice were removed, and only the long bone cartilage was retained under a dissecting microscope on ice. Total RNA was extracted with TRIzol (Life Technologies) and translated into 2 mg cDNA using SuperScript II First Strand Synthesis System (Invitrogen). In quantitative real-time polymerase chain reaction (qRT-PCR), the total of 13 μl of the reaction solution contains 6.25 μl of SYBR Green Real time PCR Master Mix (Toyobo) containing 100 nM primer and 1 μl of cDNA. CFX is connected to the real-time PCR detection system (Bio-Rad) during the reaction.

Statistical Analysis

Each experiment was repeated at least three times, and the data are expressed as the means±standard error (SEM) of the combined data from each experimental replicate. Statistical significance was evaluated by a one-way analysis of variance (ANOVA), and multiple comparisons were performed using Scheffe's method. (*) and (**) indicate $p<0.05$ and $p<0.01$, respectively, both of which are considered to be significant differences.

2. CKO-Oil and the CKO-4OHT Mice Models

Figure 1F:
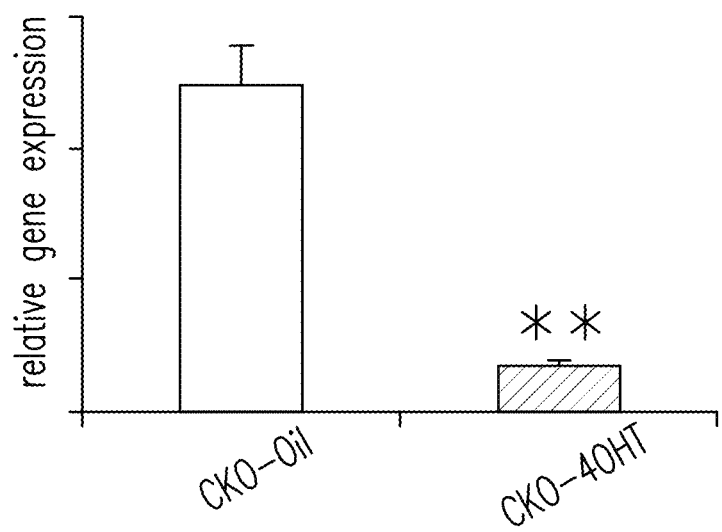
FIG. 1F shows that when compared to the control group (CKO-Oil), the gene expression of DDR-1 was significantly inhibited in CKO-4OHT mice.

To investigate whether Ddr1 deficiency affects OA progression, CKO mice injected with oil (indicated by "CKO-Oil", with normal Ddr1) and CKO mice injected with 4-OHT (indicated by "CKO-4OHT", with Ddr1 knockout) for the follow-up testing. Referring to FIGS. 1D to 1F, the gene expression and protein expression in the transgenic mice (the CKO-4OHT mice) in which the Ddr1 in chondroblasts was knocked out were inhibited and the morphology became smaller than that of the control group (the CKO-Oil mice). In addition, after staining with immunohistochemical staining (IHC), it was observed that CKO-4OHT mice with DDR1 gene knocked out did not express DDR1 (not shown in figures). Ddr1 knockout mice, which showed specific and inducible knockout of Ddr1 in chondrocytes, have the phenomena of broadened epiphyseal plate and dwarfism, which are caused by not only the decreased chondrocytes proliferation in the epiphyseal plate, but also the significant reductions of the terminal differentiation and apoptosis of the chondrocytes, thus causing reduction of angiogenesis and the entry of osteoblasts into the epiphyseal plate, and finally the reduction of ossification.

3. Intraperitoneal Injection of 4-OHT does not Affect Normal Joints and the Integrity of the Articular Cartilage in the Knockout Mice which Showed Specific and Inducible Knockout of Ddr1 in Chondrocytes.

Figure 2A:
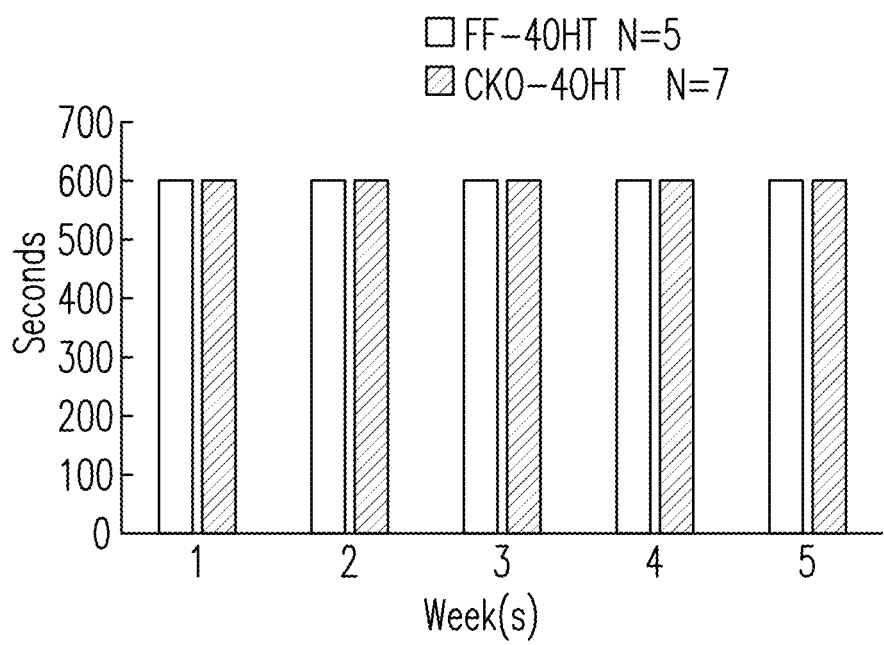
FIG. 2A shows the results of a five-week running test for the Ddr1$^{flox/flox}$ transgenic mice (the control group, expressed as "FF-4OHT") and the CKO-4OHT mice with Ddr1 deletion after intraperitoneal (IP) injection of 4-OHT.
Figure 2B:
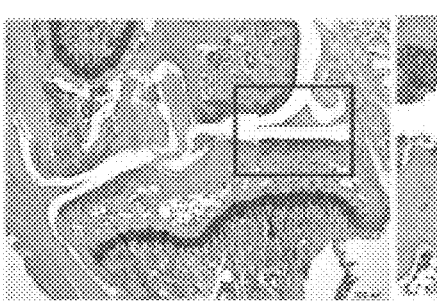
FIG. 2B shows the results of the staining by Safranin O and Fast Green in Ddr1$^{flox/flox}$ mice (the control group, expressed as "FF-4OHT") and the CKO-4OHT mice with Ddr1 deletion after IP injection of 4-OHT. Safranin O/Fast Green staining can be used to directly observe the structures of articular cartilages, subchondral bone, and bone tissue. After staining, proteoglycan is red and collagen is blue.
Figure 2B:
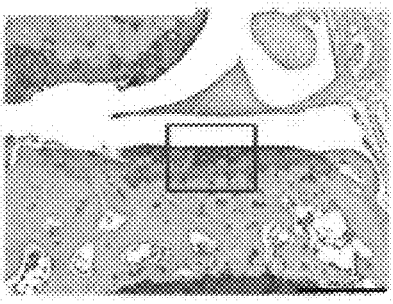
Figure 2B:
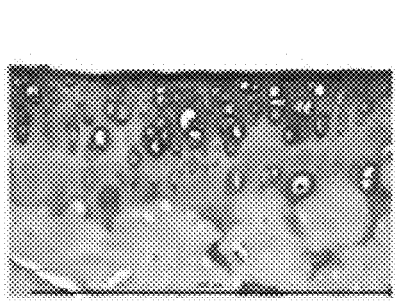
Figure 2B:
Figure 2B:
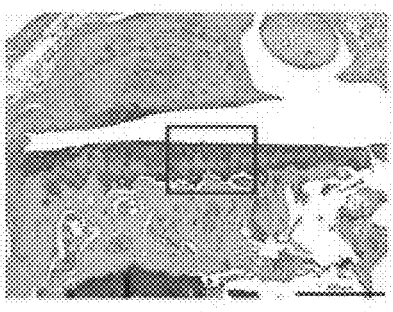
Figure 2B:
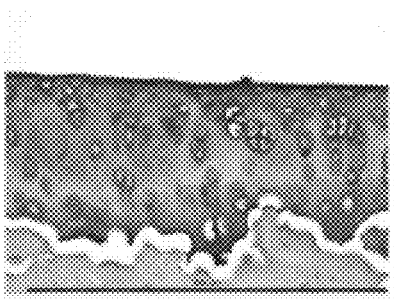

FIGS. 2A and 2B show the results of five-week running test and the results of staining with Safranin O/Fast Green in Ddr1$^{flox/flox}$ transgenic mice (the control group, expressed as "FF-4OHT") and the CKO-4OHT mice (with Ddr1 knocked out) intraperitoneally injected with 4-OHT. From the results of the five-week running test, it was found that there was no significant difference between the FF-4OHT mice and the CKO-4OHT mice. From the Safranin O/Fast Green staining results in FIG. 2B, it was confirmed that the cartilage integrity in the normal joint of CKO-4OHT mice was not affected when compared with that of the tibia of Ddr1$^{flox/flox}$ transgenic mice (the control group).

Part II. Activation of DDR1 can be Used to Prevent and Treat Abnormalities of Endochondral Ossification-Related Diseases.

1. Materials and Methods

In the relevant experiments in Part II, mice were divided into the following three groups: (1) CKO mice intraperitoneally injected with oil (hereinafter referred to as "CKO-Oil mice", which is the control group), (2) Ddr1$^{flox/flox}$ transgenic mice intraperitoneally injected with 4-OHT (hereinafter referred to as "FF-4OHT mice", which is the control group), and (3) CKO mice intraperitoneally injected with 4-OHT (hereinafter referred to as "CKO-4OHT mice"). Each group at each time point N≥6. With regard to the experiments in Part II, the materials and methods that are the same as those in Part I are not repeated.

In Part II, the chondrocytes-specific Ddr1-deficient mice (A1(II)collagen-Cre/–Ddr1$^{flox/flox}$ mice) model is used, and thereby the role of DDR1 in bone development and cartilage development can be specifically explored.

Double Staining of Alizarin Red and Alcian Blue:

1-week-old, 2-week-old, 4-week-old and 8-week-old mice were euthanized with $CO_2$. Skins and internal organs were removed from the samples, and then the sample was fixed in 95% ethanol. Then, the sample was stained with 2% Alcian blue (Alcian Blue 8GX, A5268, Sigma-Aldrich) for 2 to 3 days until the cartilage matrix of the skeleton became blue. The sample was washed with 0.5% KOH (60377, Sigma-Aldrich, LLC, Taiwan) for one month until the muscles became transparent. The sample was washed by indistillation-distillation water for 2 days and then immersed in 1% alizarin red S (A5533, Sigma-Aldrich) for 15 minutes so that the mineralized bones were stained red. The sample was washed with KOH until the muscles became completely transparent, and then observed under a microscope.

Micro Computed Tomography (Micro-CT)

Mouse tibia was scanned and 3-D reconstructed by using a High resolution micro computed tomography (micro-CT, Skyscan 1076; Skyscan NV, Kontich, Belgium). The tibia was scanned at the condition of a voltage of 44 kV, a current of 222 µA, an exposure time of 1150 ins, and a voxel size resolution of 9 µm without filters. 3-D images were reconstructed using a scale of 0-0.09 for analysis (NRecon version 1.6.1.7; Skyscan NV, Kontich, Belgium). 3-D morphometric parameters for the 2.0 mm region of the tibia ROI (4 mm circle; 100 slices) are calculated by using a direct three-dimensional method, including bone volume (BV, $mm^3$), bone volume density (BV/TV, %), bone thickness (µm), trabecular thickness (Tb.Th, µm), trabecular spacing (Tb.Sp, µm), trabecular number (Tb.N, $mm^{-1}$) and connectivity density (Con.D, $mm^{-3}$) of the cortical bone.

Tissue Morphology Analysis by H&E Staining and Safranin O/Fast Green Staining

The collected tibia was fixed with 10% formalin solution, decalcified in 1% formic acid solution at 4° C., embedded in paraffin and then cut into slices of 5 µm thickness. The slices were stained with the hematoxylin (H3136, Sigma-Aldrich) and the eosin (318906, Sigma-Aldrich) for histological analysis, or stained with 0.1% Safranin O (HT90432, Sigma-Aldrich) and 0.05% Fast Green (FCF, 2353-45-9, Sigma-Aldrich) for detecting GAG under a microscope.

TUNEL Assay

The collected tibia was fixed with 10% formalin solution, decalcified in 1% formic acid solution at 4° C., embedded in paraffin, and then cut into slices of 5 µm thickness. Apoptotic cells are detected by using in situ cell death detection kit (ab206386, Abcam) according to the protocol provided in the commercial kit. To quantify TUNEL cells, the number of brown cells was counted by Tissue FAXS, and more than 3 replicates were performed per trial.

2. Double Staining Analysis Proved the Skeletal Dysplasia of the CKO-4OHT Mice with Ddr1 Deletion During the Development of the CKO-4OHT Mice.

Figure 3A:
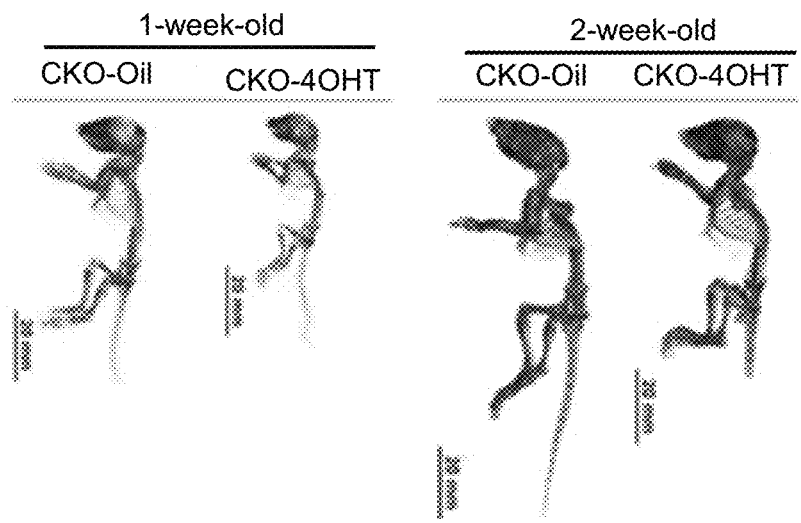
FIG. 3A shows the results of double staining of the CKO-4OHT mice and the CKO-Oil mice (the control group) of 1 week old and 2 weeks old by using Alizarin red and Alcian blue. Alizarin red can identify the location of the mineralized bone, while Alcian blue can be used to detect the proteoglycan in cartilage tissues.
Figure 3B:
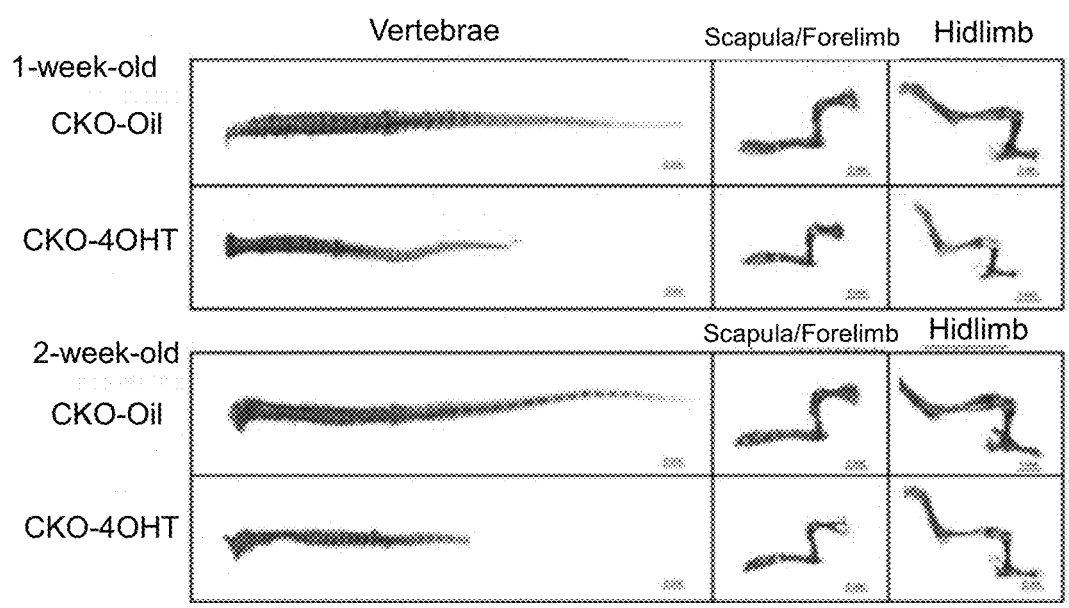
FIG. 3B shows the results of double staining of the vertebrae, scapula/forelimb and hind limbs of each group of mice in FIG. 3A.
Figure 3C:
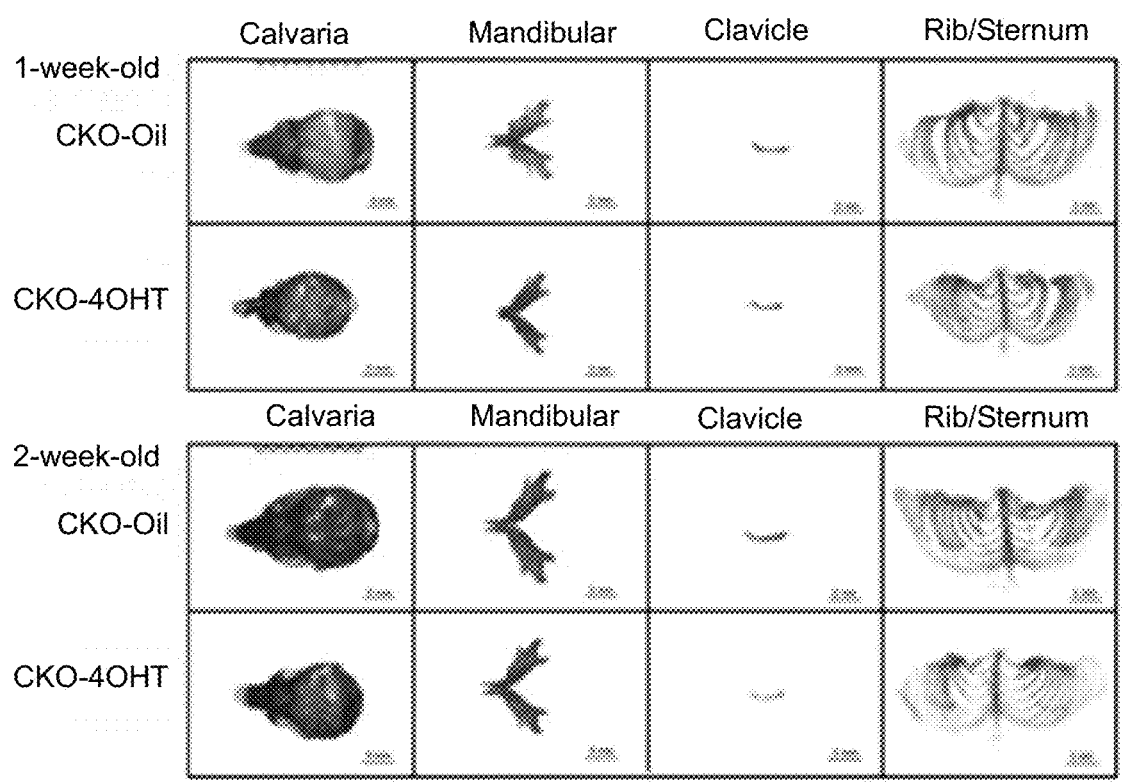
FIG. 3C shows the results of double staining of the calvaria, mandibular, clavicle and rib/sternum of each group of mice in FIG. 3A.

Histochemical analysis is often used to stain acidic polysaccharides such as cartilage and glycosaminoglycans in other body structures. In the results of Alcian Blue staining (also known as AB staining), the acidic polysaccharides around chondrocytes are dark blue or blue-violet, and the matrix is light blue. Referring to the AB staining results in FIG. 3A, in terms of appearance, no matter whether they are 1-week-old or 2-week-old mice, the body of the CKO-4OHT mice with Ddr1 deletion is significantly smaller than that of the CKO-Oil mice (the control group) of the same age. The results of the AB staining in FIGS. 3B and 3C show that in the long bones (such as the tibia, the femur, etc.), the cartilage distribution area, which is stained by Alcian Blue and thus is dark blue or blue-violet, of the CKO-4OHT mice is larger than that of the control group. In addition, after dismantling all joints, it can be observed that various bones of the CKO-4OHT mice were smaller and shorter than the control group, and this result showed that the ossification of the CKO-4OHT mice was incomplete. Actually, during the development, from 2-week-old to 10-week-old, of the CKO-4OHT mice, either the appearance or the bone components (including the clavicle, ribs, spine, upper limbs and lower limbs) showed a tendency of delayed growth and development.

3. The Knockout of Ddr1 in Chondrocytes Delays the Development of the Secondary Ossification Center in Femur and Tibia.

Figure 4A:
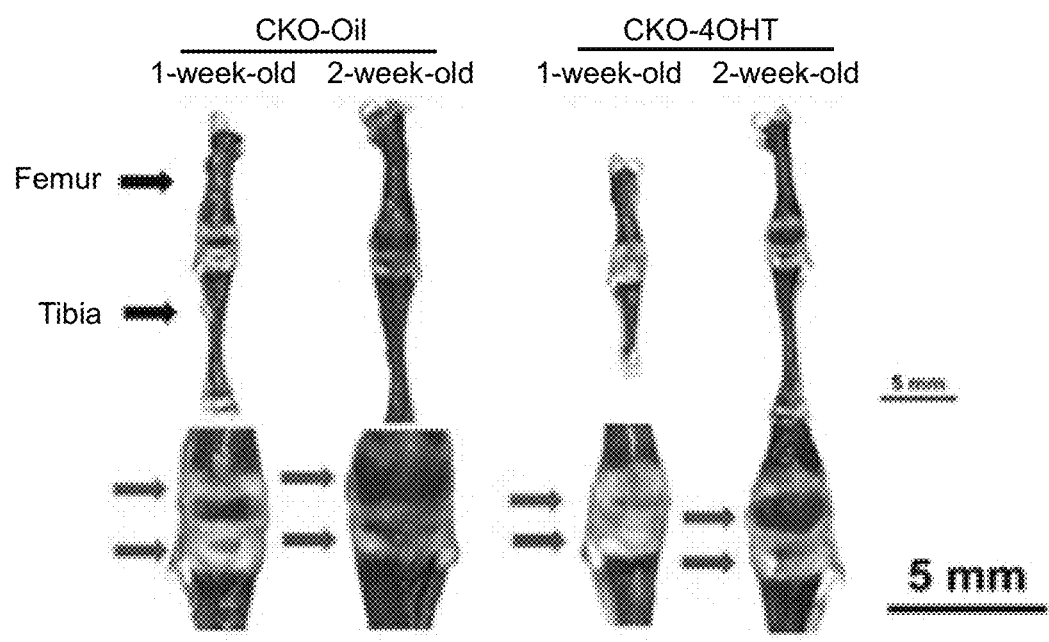
FIG. 4A shows the secondary ossification centers of the femur and tibia of the 1-week-old and 2-week-old CKO-4OHT mice and CKO-Oil mice (the control group) (wherein in the enlarged portion at the bottom of the figure, the upper arrow indicates the secondary growth zone of femur, and the down arrow indicates the secondary growth zone of the tibia).

During the development of bones, long bones (such as vertebrae, forelimb, metacarpal and hindlimb) are formed and developed through the endochondral ossification process, and in the long bones, a secondary ossification center is formed. FIG. 4A shows the secondary ossification centers of femur and tibia of the 1-week-old and 2-week-old CKO-4OHT mice and CKO-Oil mice (the control group), in which the upper arrow indicates the secondary growth zone of femur, and the lower arrow indicates the secondary growth zone of tibia. As shown in FIG. 4A, the secondary ossification center (as indicated by the arrow) in femur and tibia can be seen in the 1-week-old CKO-Oil mice (the control group), while in the 1-week-old CKO-4OHT mice, the secondary ossification center (as indicated by the arrow) is absent or the cells therein is dead, and the development of the secondary ossification center in the 2-week-old CKO-4OHT mice is also delayed. These results show that the knockout of Ddr1 in chondrocytes delays the development of the secondary ossification center in femur and tibia.

4. Endochondral Ossification of Tibia of the CKO-4OHT Mice is Delayed.

Figure 4B:
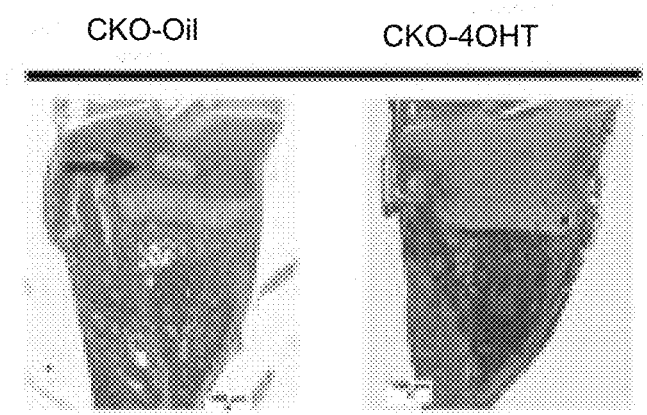
FIG. 4B shows the staining results of cartilage of the proximal tibia of the 1-week-old CKO-4OHT mice and the 1-week-old CKO-Oil mice (the control group) by using H&E staining. The arrow indicates the secondary ossification center.
Figure 4C:
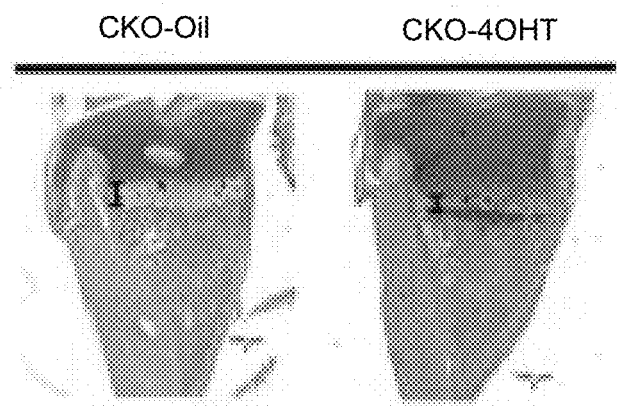
FIG. 4C shows the results of Safranin O/Fast Green staining of cartilage in the proximal tibia of the 1-week-old CKO-4OHT mice and the 1-week-old CKO-Oil mice (the control group). After staining, the proteoglycan (representing the cartilage area) is red, and collagen is blue. The I-shape black line shows the thickness of the hypertrophy zone of the proximal tibia of the CKO-4OHT mice and the CKO-Oil mice.

To evaluate the endochondral ossification during the development, tibia of the 1-week-old mice was collected, fixed with 10% formalin solution, embedded in paraffin, and then cut into slices having a thickness of 5 µm. The samples were stained with hematoxylin and eosin (H & E) and Safranin O/Fast Green. FIGS. 4B and 4C show the staining results of cartilage of the proximal tibia of the 1-week-old CKO-4OHT mice and CKO-Oil mice (the control group) by using hematoxylin and eosin (H&E) or Safranin O/Fast Green staining. In the proximal tibia of the 1-week-old CKO-4OHT mice, the region stained with Alcian Blue (the cartilage area) is significantly larger than that in the control group. Secondary ossification center (as shown by the arrow in FIG. 4B) can be clearly seen in the middle of the cartilage of the proximal tibia of the 1-week-old CKO-Oil mice, but no secondary ossification center was observed in the middle of the cartilage in the CKO-4OHT mice. The staining results of Safranin O/Fast Green are shown in FIG. 4C, in which the proteoglycan (representing the cartilage area) is red, and collagen is blue. The staining results of Safranin O/Fast Green show that the proximal tibia of CKO-4OHT mice had a denser sGAG staining (proteoglycan) and a longer cartilage region (red) than the CKO-Oil mice (the control group), which indicates that in the CKO-4OHT mice, the chondrocytes that synthesize proteoglycans in extracellular matrix may be more active than that in the CKO-Oil mice (the control group). In contrast, the hypertrophy zone in the proximal tibia of CKO-4OHT mice is smaller than the hypertrophy zone of the CKO-Oil mice (shown by the I-shape black line in FIG. 4C).

Figure 4D:
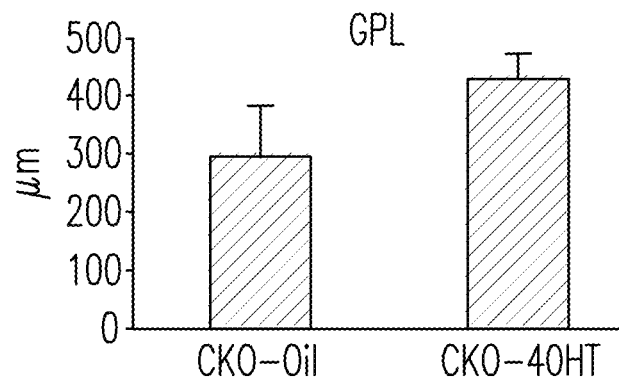
FIG. 4D shows the epiphyseal plate length (GPL) measured after staining of the tibia of the 4-week-old CKO-4OHT mice and the 4-week-old CKO-Oil mice (the control group) with Safranin O/Fast Green.
Figure 4E:
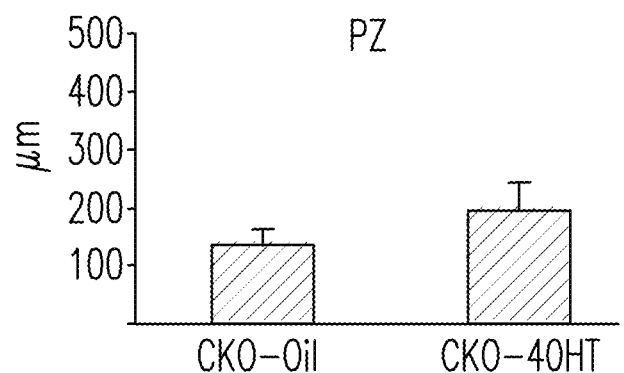
FIG. 4E shows the thickness of the proliferation zone (PZ) measured after staining of the tibia of the 4-week-old CKO-4OHT mice and the 4-week-old CKO-Oil mice (the control group) with Safranin O/Fast Green.
Figure 4F:
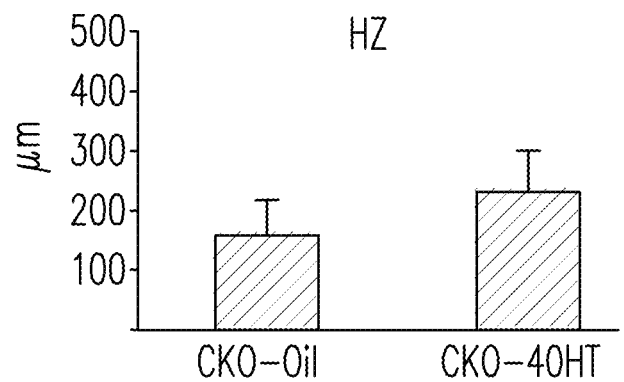
FIG. 4F shows the thickness of the hypertrophy zone (HZ) measured after staining the tibia of the 4-week-old CKO-4OHT mice and the CKO-Oil mice (the control group) with Safranin O/Fast Green.

FIGS. 4D to 4F show the epiphyseal plate length (GPL), the thickness of the proliferation zone (PZ) and the thickness of the hypertrophy zone (HZ) measured after staining the tibia of the 4-week-old CKO-4OHT mice and the CKO-Oil mice (the control group) with Safranin O/Fast Green. As shown in FIG. 4D, through further analysis of the epiphyseal plate, it was found that in the hypertrophy zone in the tibia of the 4-week-old CKO-4OHT mice, the length of the epiphyseal plate was increased and there were increased irregular cells.

Figure 5A:
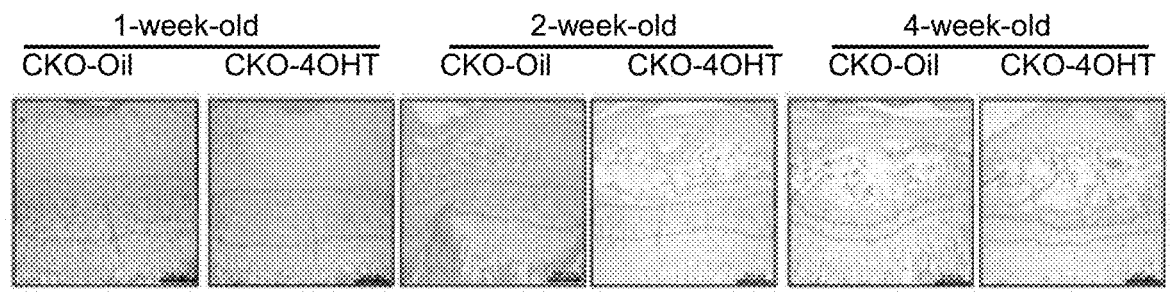
FIG. 5A shows Ki-67 immunohistochemical staining of the tibia epiphyseal plate in the 1-week-old, 2-week-old and 4-week-old CKO-4OHT mice and CKO-Oil mice (the control group) to observe the proliferation zone (which is between two dotted lines). Magnification is 100 times and the scale bar is 250 μm.
Figure 5B:
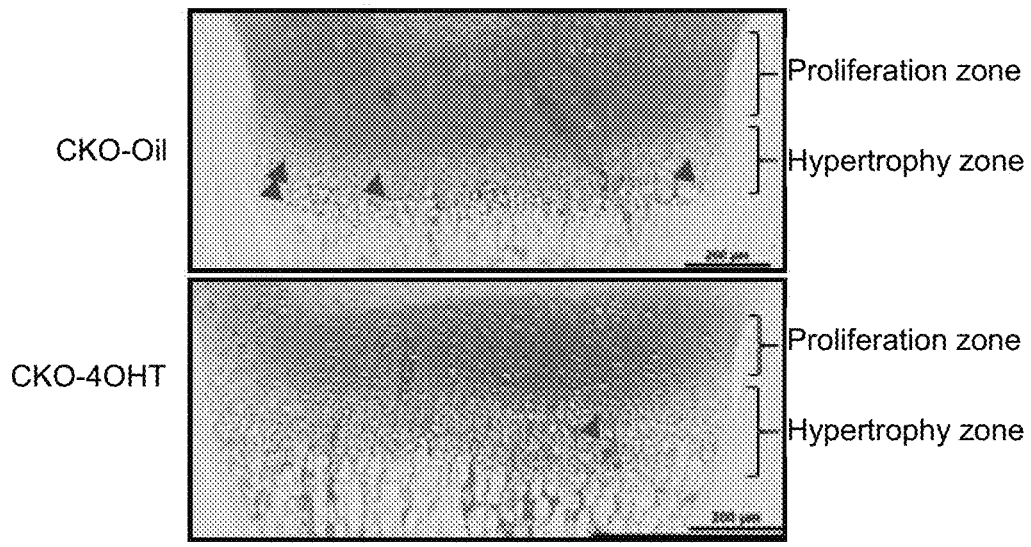
FIG. 5B shows the detection of apoptotic cells in the chondrocytes in the tibia epiphyseal plate of the 1-week-old CKO-4OHT mice and CKO-Oil mice by the TUNEL assay.
Figure 5C:
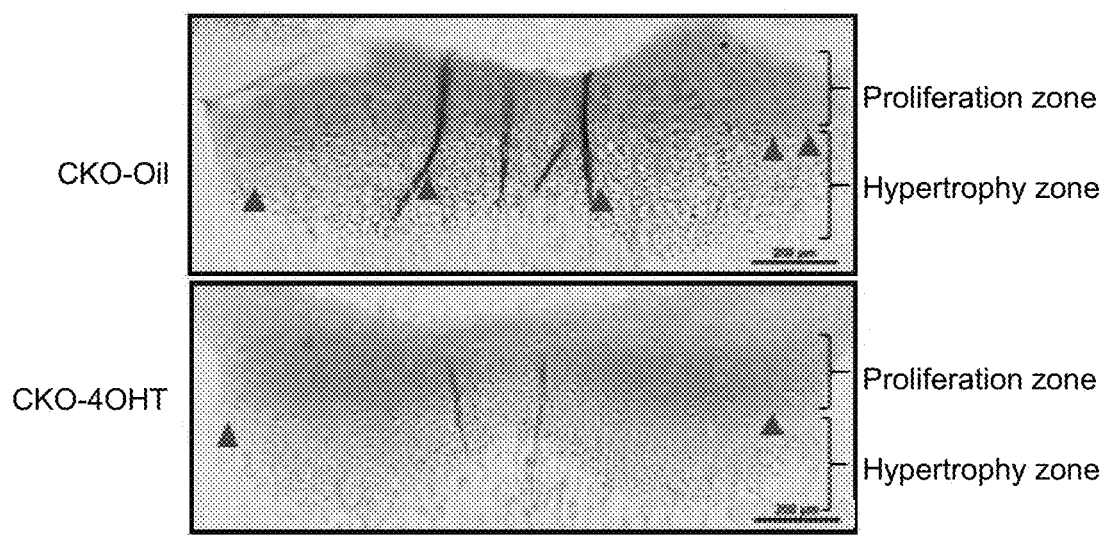
FIG. 5C shows the detection of apoptotic cells (as indicated by black dots) in the chondrocytes in the tibia epiphyseal plate of the 2-week-old CKO-4OHT mice and the 2-week-old CKO-Oil mice by the TUNEL assay.

Since more chondrocytes appear in the proliferative and hypertrophic regions, further analysis is performed to realize whether there is the increased proliferation, the decreased cell death, or both for the chondrocytes. Ki-67 immunohistochemical staining can be used to assess the percentage of total proliferating cells at all active phases of the cell cycle. Referring to the proliferation zone between the two dotted lines shown in FIG. 5A, the Ki67 staining revealed that, compared to the 1-week-old to 4-week-old CKO-Oil mice, there is less staining in the proliferation zone in the tibia epiphyseal plate of the CKO-4OHT mice. That is, there is a sharper decrease in the progression zone of the CKO-4OHT mice than that in the proliferation zone of the CKO-Oil mice. This result indicates that the increased chondrocytes in the epiphyseal plate of the CKO-4OHT mice are not derived from the proliferation that occurred in the proliferation zone. Therefore, the inventors examined apoptosis by the TUNEL assay that detects the DNA fragments by labeling nucleic acid ends, thereby evaluating the death of chondrocytes. FIG. 5B and FIG. 5C show the detection of apoptotic cells (shown by black dots) in the epiphyseal plate of the tibia of the 1-week-old and 2-week-old CKO-4OHT mice and CKO-Oil mice, respectively, by using the TUNEL assay. As can be seen from the detection results of the 2-week-old mice in FIG. 5C, the TUNEL staining in the hypertrophy zone of the CKO-4OHT mice was less than that in the CKO-Oil mice (as indicated by the arrows in FIG. 5C). As can be seen from FIGS. 5A to 5C, the knockout of Ddr1 reduces terminal differentiated chondrocytes during bone development.

The endochondral ossification is regulated by the feedback loop, including parathyroid hormone-related protein (PTHrP), Indian hedgehog (Ihh) and Bcl-2 JTHrP in the epiphyseal plate, which maintain the function of proliferating chondrocytes and inhibit the differentiation of chondrocytes into hypertrophy cells. The cartilages of the 4-5-day-old CKO-4OHT mice and CKO-Oil mice were obtained to detect the expression of Collagen type X, Ihh protein and PTHrP gene.

Figure 6A:
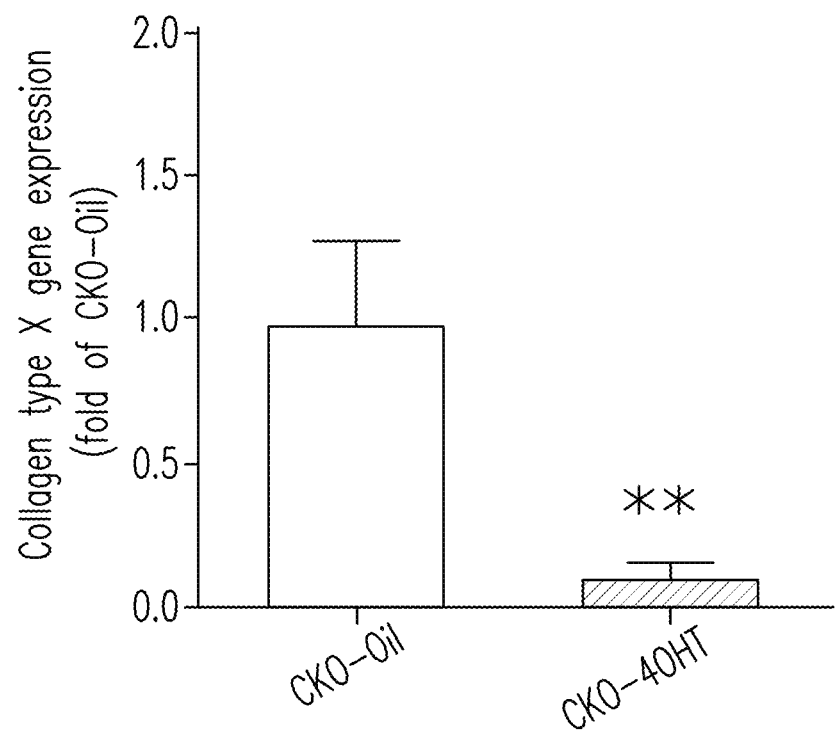
FIG. 6A shows the expression of the collagen type X gene in cartilages of the CKO-4OHT mice and the CKO-Oil mice 4-5 days after birth. ** indicates p<0.01 as compared to the CKO-Oil group.

The relative amount of mRNA was calculated by the cycle threshold (Ct) value of each PCR product and normalized to the level of GAPDH using the comparative Ct method. The relative value of the gene expression of the control CKO-Oil mice was set to 1 and all other amounts were converted to ratios. As shown in FIG. 6A, the collagen type X of CKO-4OHT mice was significantly reduced as compared to the collagen type X of the CKO-Oil mice. Furthermore, as compared to the CKO-Oil mice, the Ihh gene expression of CKO-4OHT mice was significantly reduced while the PTHrP gene expression of CKO-4OHT mice was significantly increased to more than four times (not shown).

Figure 6B:
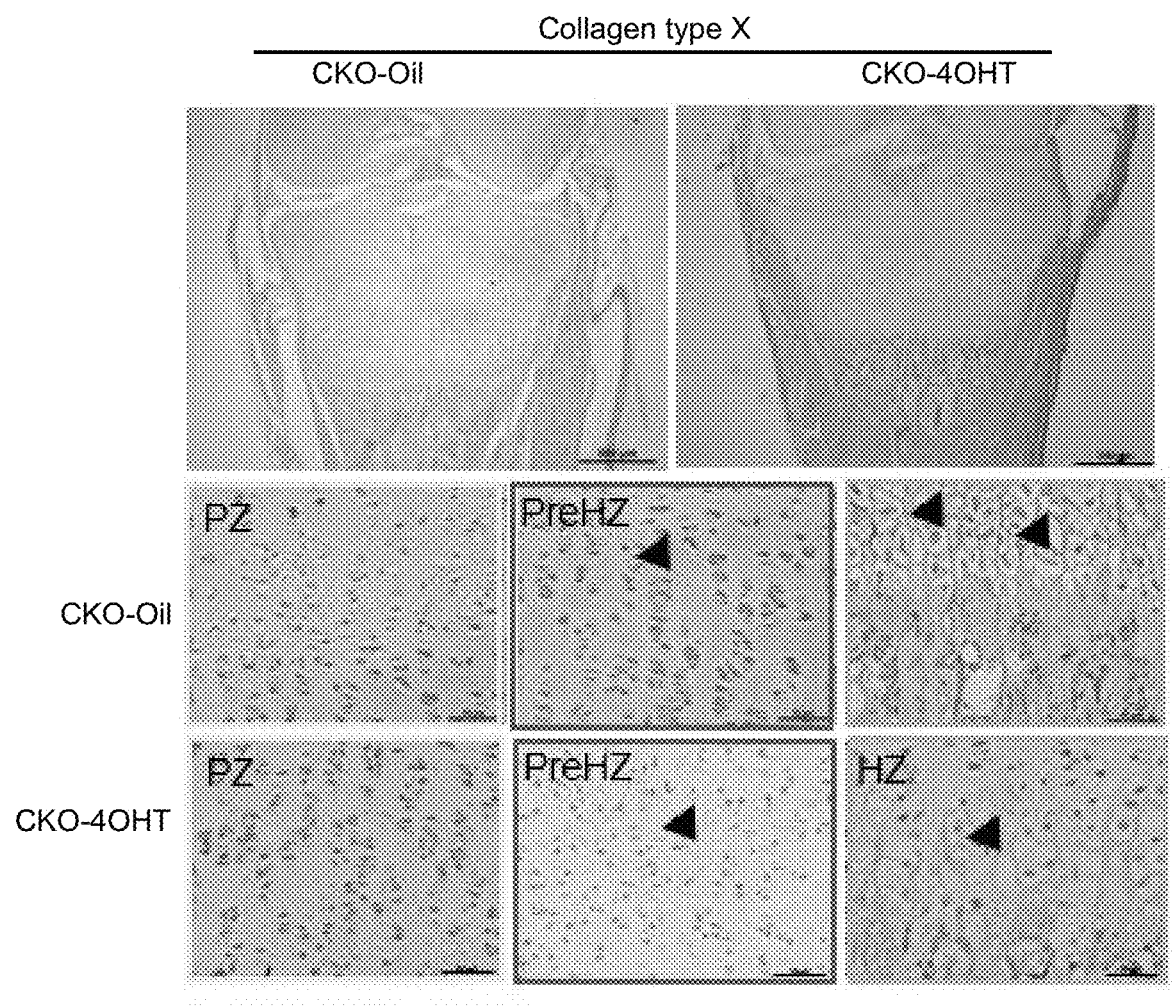
FIG. 6B shows the staining results of the tibia of the 1-week-old CKO-4OHT mice and the 1-week-old CKO-Oil mice by using immunohistochemistry staining and counterstaining with hematoxylin, which are observed under a microscope. PreHZ represents the pre-hypertrophic zone; HZ represents the hypertrophy zone; PZ represents the proliferation zone; and the arrows indicate the chondrocytes.

FIG. 6B shows the immunohistochemistry staining of the tibia of the 1-week-old CKO-4OHT mice and the CKO-Oil mice. Collagen type X is a chondrogenesis marker of the cartilage extracellular matrix. It can be seen from FIG. 6B that the collagen type X stain in proliferation zone (HZ) of CKO-4OHT mice can reduce the extracellular matrix of the pre-proliferation zone (PreHZ) (as indicated by the arrow) and the chondrocytes (as indicated by the arrow). In view of the fact that Ihh will feedback control the release of PTHrP during the endochondral ossification, the Ihh staining showed that the expression in the hypertrophy zone of CKO-4OHT mice was significantly lower than that of the control group (not shown). In addition, PTHrP in the proliferation zone of CKO-4OHT mice was increased (not shown). From the above, it was found that the collagen type X staining in the CKO-4OHT group mice was less than that for the 2-week-old CKO-Oil mice. These results indicate that the knockout of Ddr1 may delay the terminal differentiation of chondrocytes in the proliferation zone, which in turn leads to a delay in the endochondral ossification of the tibia of the 4-OHT-injected mice of the CKO-4OHT group. Furthermore, the length of the epiphyseal plate in the CKO-4OHT mice increased due to less chondrocyte apoptosis and no increase in proliferating cells. As a result, the chondrocytes in the epiphyseal plate of the CKO-4OHT mice had less apoptosis and less terminal differentiation.

5. Quantification of Skeletal Dysplasia of Tibia of the CKO-4OHT Mice Using Micro Computed Tomography (Micro-CT).

Figure 6C:
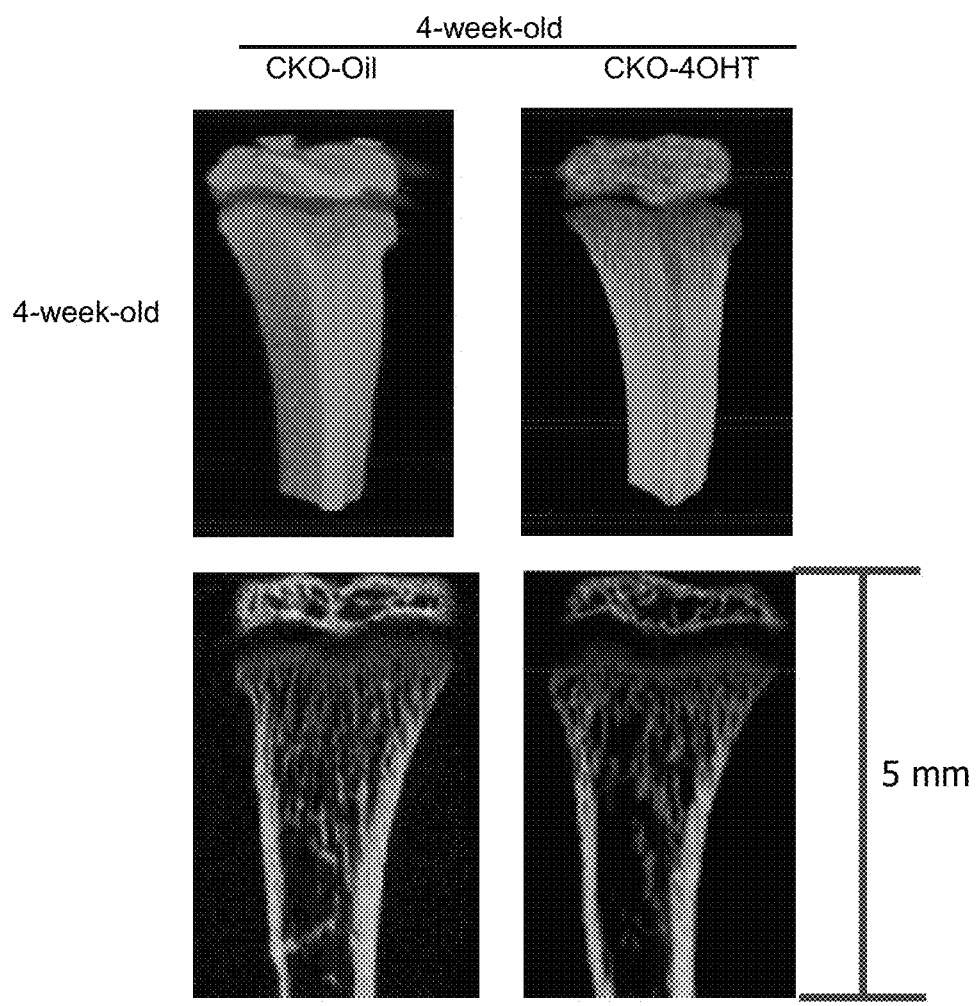
FIG. 6C shows the three-dimensional skeletal structure of the tibia of the 4-week-old CKO-4OHT mice and the 4-week-old CKO-Oil mice (the control group) observed using micro CT (micro computed tomography) with high-resolution. The upper two figures show three-dimensional views, and the lower two figures are cross-sectional views.
Figure 6D:
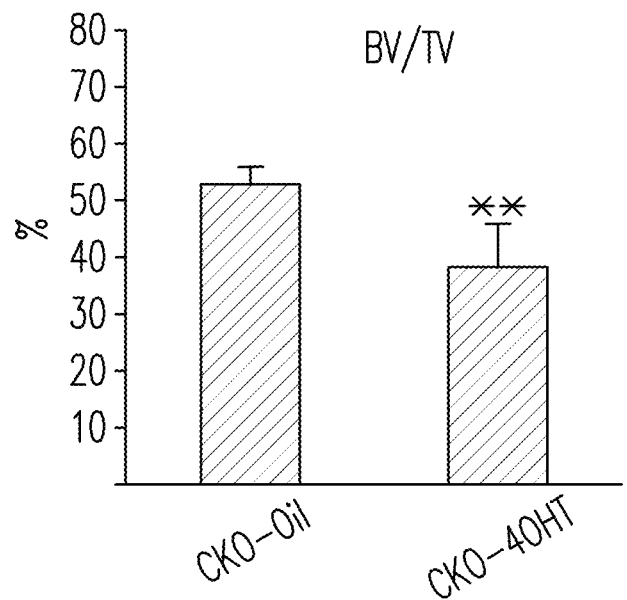
FIG. 6D shows the bone volume/total volume (BV/TV, %) of the cortical bone of the tibia in the 4-week-old CKO-4OHT mice and the 4-week-old CKO-Oil mice (the control group).
Figure 6E:
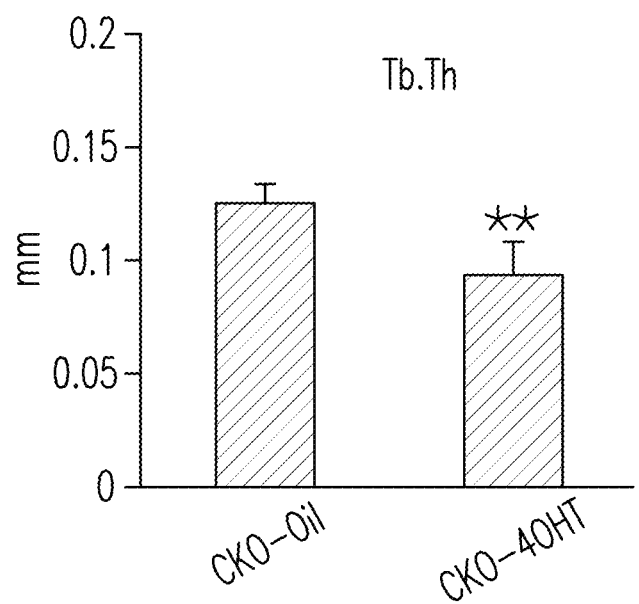
FIG. 6E shows the trabecular thickness (Tb.Th) of the tibia in the 4-week-old CKO-4OHT mice and the 4-week-old CKO-Oil mice (the control group).
Figure 6F:
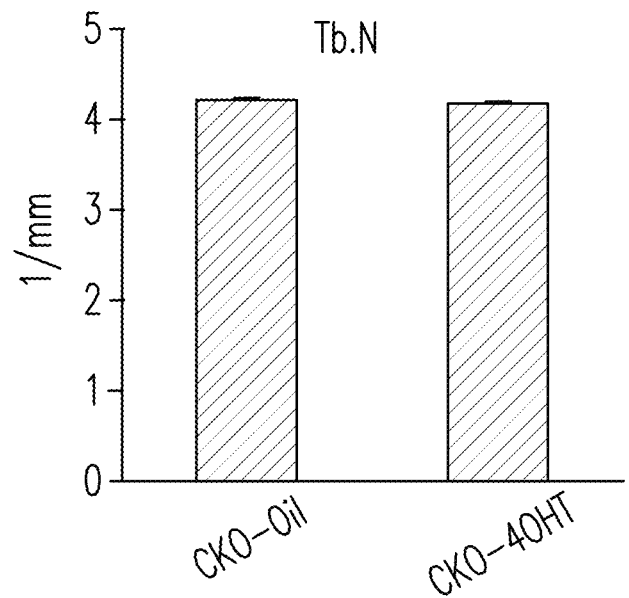
FIG. 6F shows the trabecular number (Tb.N) of the tibia in the 4-week-old CKO-4OHT mice and the 4-week-old CKO-Oil mice (the control group).
Figure 6G:
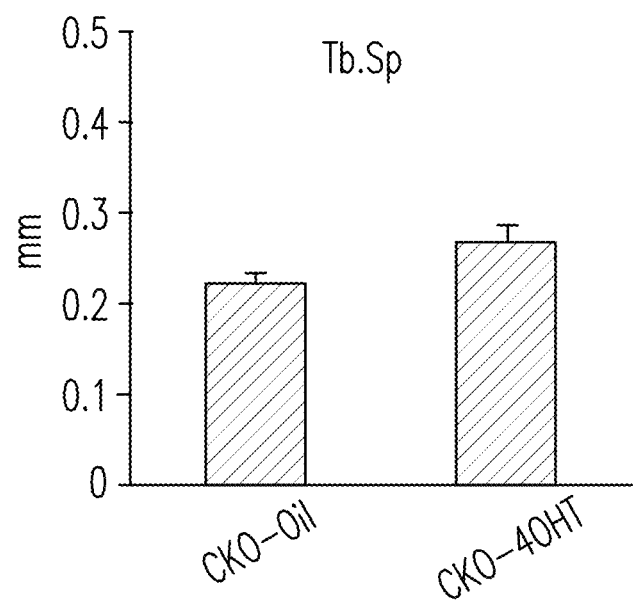
FIG. 6G shows the trabecular spacing (Tb.Sp) of the tibia in the 4-week-old CKO-4OHT mice and the 4-week-old CKO-Oil mice (the control group).

The three-dimensional micro-structures of the tibias of the 4-week-old CKO-4OHT mice and the CKO-Oil mice (the control group) were analyzed by using high resolution micro-CT, and the results are shown in FIG. 6C. The 3-D micro-CT images of the tibias were reconstructed and the 3-D morphological parameters were calculated. In tibia, the reconstructed 3-D images including the three-dimensional view (the top right part in FIG. 6C) and the cross-sectional view (the bottom right part of FIG. 6C) of the CKO-4OHT mice show that the size of the CKO-4OHT mice is smaller than that of the CKO-Oil mice (the control group). In addition, the average space for the tibia of the CKO-4OHT mice is reduced. As compared with the CKO-Oil mice (the control group), the tibia of the CKO-4OHT mice showed a significant decrease in the percentage of bone volume/total volume of the cortical bone (BV/TV, i.e., the bone volume density) and the trabecular thickness (Tb.Th), while there is no significant difference for the trabecular number (Tb.N) and the trabecular spacing (Tb.Sp) (as shown in FIG. 6D to FIG. 6G). It can be known from the above results that the knockout of the Ddr1 gene in chondroblasts reduced BV/TV and trabecular thickness, but did not affect the trabecular number and the trabecular spacing. The above evidences reveal that the knockout of DDR1 will make the structure of the bone more fragile and cause the issue of osteoporosis.

The experiments related to Part II show the following results (shown by FIG. 3A to FIG. 6G). During skeletal development, DDR1 positively regulates the function of chondrocytes during intramembranous ossification and endochondral ossification. The deletion of the Ddr1 gene in chondrocytes inhibits the degeneration of chondrocytes into hypertrophic chondrocytes and keep the chondrocytes to accumulate in the cartilage area without forming hard bones via calcification, which result in abnormalities of endochondral ossification (achondroplasia) and thus skeletal growth retardation. Therefore, DDR1 gene knockout can cause the dwarfism type mouse and the achondroplasia mouse with abnormalities of skeletal growth. Further mechanism investigation results show that the knockout of DDR1 inhibits chondrocyte degeneration, hypertrophy and apoptosis, which lead to abnormal bone development and achondroplasia. The experiment results reveal that DDR1 plays an important role in the early and late stages of bone and cartilage development. By regulating the associated pathways activating DDR1, it can be used to prevent or even treat bone abnormalities in dwarfism and achodroplasia. Since the expression of the normal Ddr1 gene (the control group) can cause the normal endochondral ossification to proceed and thus achondroplasia and skeletal growth retardation will not occur, the abnormalities of endochondral ossification and achondroplasia can be prevented or treated by gene therapy, preparation agents or preparation antibodies associated with the application of activating DDR1 pathway.

Part III. The Relationship of DDR1 and Bone-Loss Related Diseases or Conditions.
1. Materials and Methods With regard to the experiments in Part III, the materials and methods that are the same as those in Part I or Part II are not repeated.

OKOΔDdr1 Mice

The 4-OHT was dissolved in DMSO to generate a stock solution at a concentration of 25 mg/mL, and the working concentration was 4 mg/kg diluted in corn oil at an oil:4-OHT ratio of 9:1. This 4-OHT solution was intraperitoneally injected into E14.5 mice (4 mg/kg/day) along with progesterone (2 mg/day/kg; P0130, Sigma-Aldrich). After birth, 1 mg/kg 4-OHT was injected per day for 5 consecutive days. Then, 2-week-old and 4-week-old mice were collected. $Ddr1^{flox/flox}$ transgenic mice injected with 4-OHT hereinafter are referred to as "$Ddr1^{f/f-4OHT}$" or "FF-4OHT". Both $Ddr1^{f/f-4OHT}$ (control group) and OKOΔDdr1 (experimental group) mice were injected with 4-OHT on the abovementioned schedule.

OKO-4OHT Mice 1 mg/kg 4-OHT solution was intraperitoneally injected into mature mice for 3 consecutive days per week from 7-week-old to 10-week-old and then one dose per week until sacrificed at 16 week-old.

Ovariectomy (OVX) Mice and Sham Mice

Ovariectomy (OVX) was performed on 8-week-old female mice. The experimental groups and the positive control group of the mice underwent anesthesia and were ovariectomized through their back for both sides of the ovaries. For the sham operation group, which was used as a control group, ICR mice's abdominal cavities were cut but their ovaries were not removed. After the recovery period of 1 to 2 weeks after the bilateral ovariectomy, mice were randomly assigned to different treatment groups. When the mice were sacrificed, the ovarian tissues were checked to confirm whether the removal of ovarian was successful. The mice with unsuccessful ovariectomies were not used in the subsequent experiments.

Cell Culture and Drug Treatment

The mouse preosteoblast cell line MC3T3-E1 (CRL-2593) (ATCC, Manassas, VA, USA) was grown in α-minimal essential (α-MEM) medium supplemented with 10% fetal bovine serum (FBS) and 100 units/mL penicillin and was maintained at 37° C. with 5% $CO_2$. SB203580 (Cilio-brevin A, Selleckchem, Houston, TX, USA), an inhibitor of phosphorylated p38, was dissolved in DMSO as a stock solution, and the cells were treated with the inhibitor at a final concentration of 20 μM for 16 h, after which the cells were harvested for Western blot analysis.

Lentivirus Constructs and Transfection

Lentivirus was used to transiently knock down or overexpress Ddr1 in MC3T3-E1 cells. Purchased lentivirus particles with shLacZ (as control), shDdr1 (as knockdown Ddr1, TRCN0000010084), vehicle (as a control for Ddr1 overexpression, PLAS2W.Pp), and ovDdr1 (as overexpress Ddr1, PLAS2W.DDR1.Pp) from the RNAi Core Facility of Taiwan. MC3T3-E1 cells were cultured in 10 cm dishes at a density of $1\times10^6$, infected lentivirus particles for 16 h (MOI of 1) and used puromycin (2 μg/mL) to select stable cell lines.

Real-Time PCR (qPCR) Analysis

MC3T3-E1 cells were treated with SB203580 for 24 hr and the in vivo calvarial bone was extracted from postnatal 4-day-old to 5-day-old $Ddr1^{f/f-4OHT}$ and OKOΔDdr1 mice and placed on ice. The PureLink RNA mini kit (Thermo Fisher Scientific Inc., Waltham, MA, USA.) was used to obtain total RNA, and then cDNA was transcribed from 2 μg of total RNA with the Verso 1-Step RT-PCR Kit ReadyMix with ThermoPrime Taq. For quantitative real-time PCR, 6.25 μL of SYBR (BIO-RAD Laboratories Inc., Hercules, CA, USA), 1 μL of cDNA, 0.5 μL of specific primers, and $ddH_2O$ to a total volume of 13 μL were mixed and run on a CFX connect real-time PCR detection system (BIO-RAD Laboratories Inc., Hercules, CA, USA). GAPDH was used as a housekeeping gene, and expression was normalized to that in $Ddr1^{f/f-4OHT}$ mice.

Three-Point Bending Test

The 4-week-old mouse femurs were subjected to 3-point bending and tested to failure by using a materials testing system (INSTRON 5943, Norwood, MA, USA). The femur was placed on 2 lower supports 2 mm apart. The load was placed at the middle of the femur at a displacement rate of 0.05 mm/s until failure. Quantitative analysis was performed with Bluehill software (Illinois Tool Works Inc., Glenview, IL, USA).

Statistical Analysis

All animal experiments are expressed as the mean (SEM) of 6 independent groups. Each condition was repeated at least three times, and the total number of mice per group was more than 6. Statistical significance was determined using Student's t-test, and multiple comparisons were performed using Scheffé's method. In Part III, the groups were compared with the $Ddr1^{f/f-4OHT}$ group. For the p values, (*) indicated p<0.05, and () indicated p<0.01, and (*) indicated p<0.001.

2. Basic Study for OKO-4OHT Mice

Figure 7A:
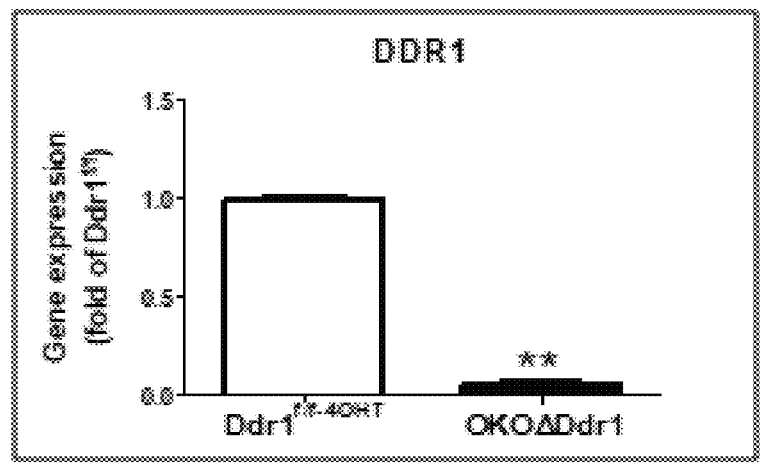
FIGS. 7A and 7B show (A) gene expression and (B) protein level of Ddr1 in calvarial bone of Ddr1$^{f/f-4OHT}$ and OKOΔDdr1 mice, wherein the calvarial bone was extracted on postnatal days 4~5.
Figure 7B:
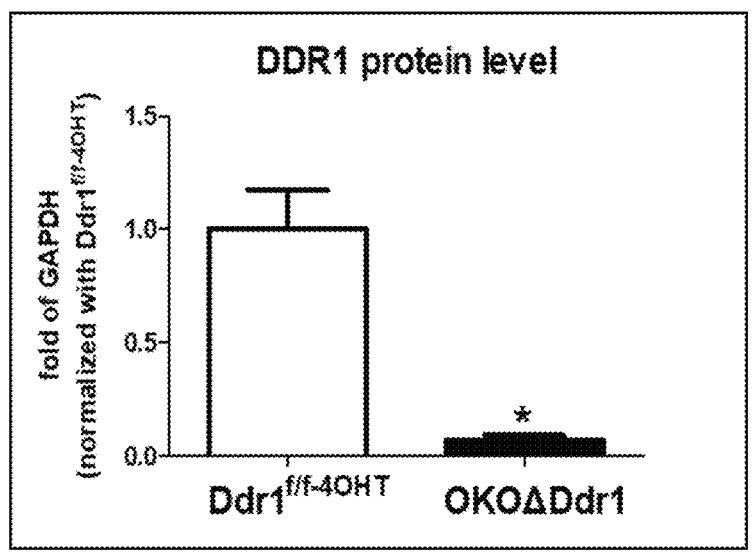
Figure 7C:
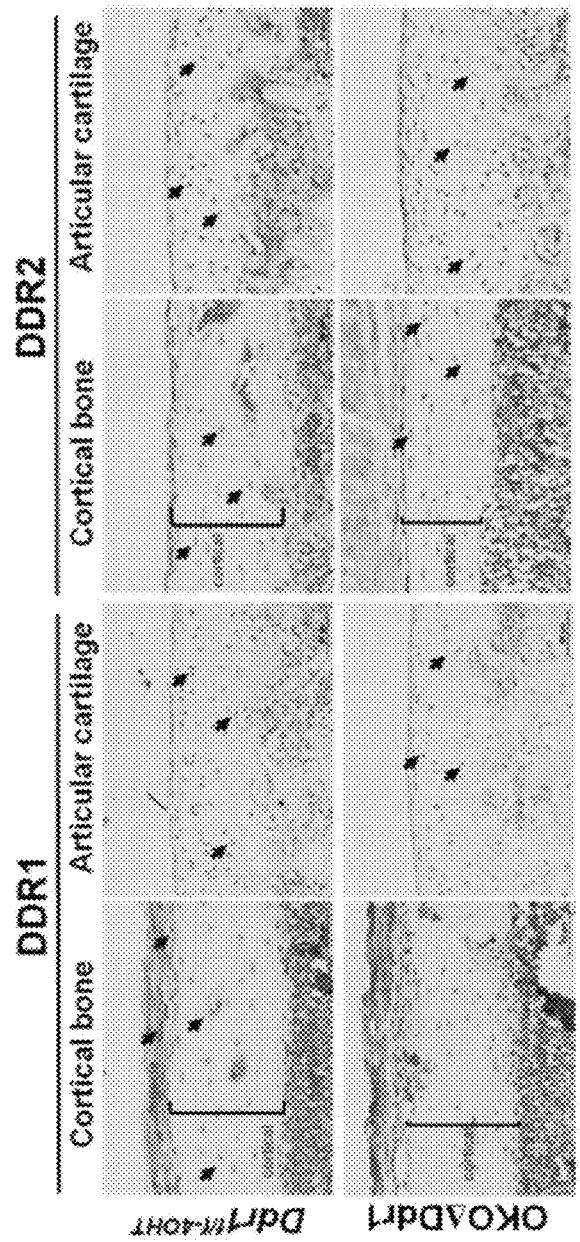
FIG. 7C shows IHC staining of DDR1 and DDR2 in cortical bone and articular cartilage of femurs from 4-week-old mice. Black arrow indicates DDR1-positive cells, and black frame indicates the cortical region.
Figure 7D:
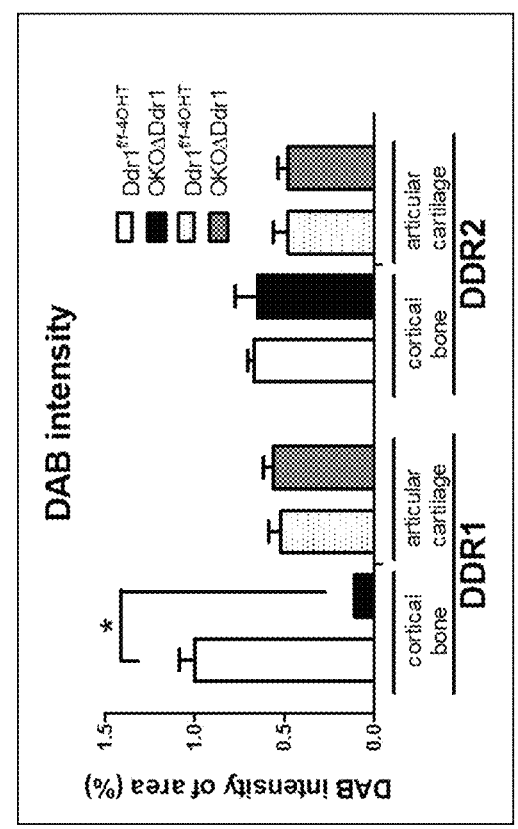
FIG. 7D shows quantitative results by tissue faxes normalized with Ddr1$^{f/f-4OHT}$. Magnifications of 400× are shown, with scale bars of 50 μm. Each group n≥6. * indicates p≤0.05 and ** indicates p≤0.01.

To investigate the role of Ddr1 in osteoblasts during bone ossification, the inventors first generated 4-OHT inducible osteoblast-specific Ddr1 knockout (a1(I)-CreERT; $Ddr1^{flox/flox}$) mice on the OKO background. To confirm the osteoblast-specific knockout of Ddr1 in OKOΔDdr1 mice, the inventors conducted gene expression, Western blot, and IHC staining assays in $Ddr1^{f/f-4OHT}$ and OKOΔDdr1 mice. The qPCR results showed that the gene expression of Ddr1 in OKOΔDdr1 mice was significantly decreased by approximately 95% compared with that in $Ddr1^{f/f-4OHT}$ mice (FIG. 7A). Additionally, the protein level of DDR1 was decreased by approximately 90% in OKOΔDdr1 mice compared with $Ddr1^{f/f-4OHT}$ mice (FIG. 7B). To further demonstrate that the inventors specifically knocked out Ddr1 in osteoblasts, IHC staining was performed for DDR1 in the femurs of 4-week-old mice, the results of which showed that DDR1 staining was obvious in the cortical bone, periosteum and articular chondrocytes in $Ddr1^{f/f-4OHT}$ mice. However, DDR1 staining was decreased by approximately 90% in cortical bone in OKOΔDdr1 mice but was still observed in articular chondrocytes (FIGS. 7C and 7D). By contrast, DDR2 staining in cortical bone and articular chondrocytes was similar in $Ddr1^{f/f-4OHT}$ and OKOΔDdr1 mice and showed no significant quantitative difference (FIGS. 7C and 7D). These results indicated that the success in the creation of osteoblast-specific Ddr1 knockout (OKOΔDdr1) mice and that this model did not affect the expression of Ddr2, suggesting that there is no compensatory effect of Ddr2 expression. The osteoclasts were stained by TRAP staining, and immunochemistry stain of TRAcP was as an osteoclast marker. The results showed that knockout Ddr1 in osteoblasts had no effect on osteoclast activity and the expression of osteoblasts (not shown in the figures). The above results indicated that knockout Ddr1 in osteoblasts would not influence the osteoclast phenotype, and demonstrated the osteoblast-specific Ddr1 knockout in mice.

Figures 8A, 8C:
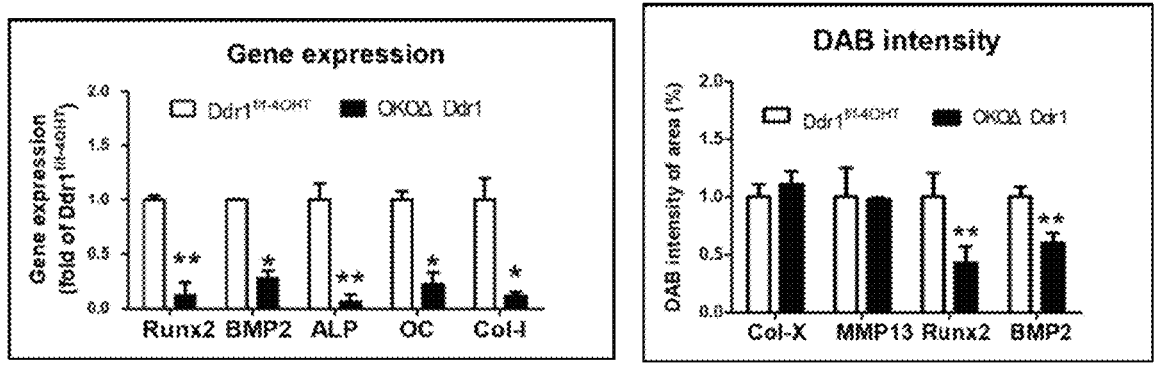
FIG. 8A shows the gene expression of markers related to osteogenesis (Runx2, BMP2, ALP, OC, and Col-I) in calvarial bone of Ddr1$^{f/f-4OHT}$ and OKOΔDdr1 mice.
FIG. 8C shows Quantitation of Col-X, MMP13, Runx2, and BMP2 expression in the trabecular area. Each group n≥6; * p≤0.05, ** p≤0.01.
Figure 8B:
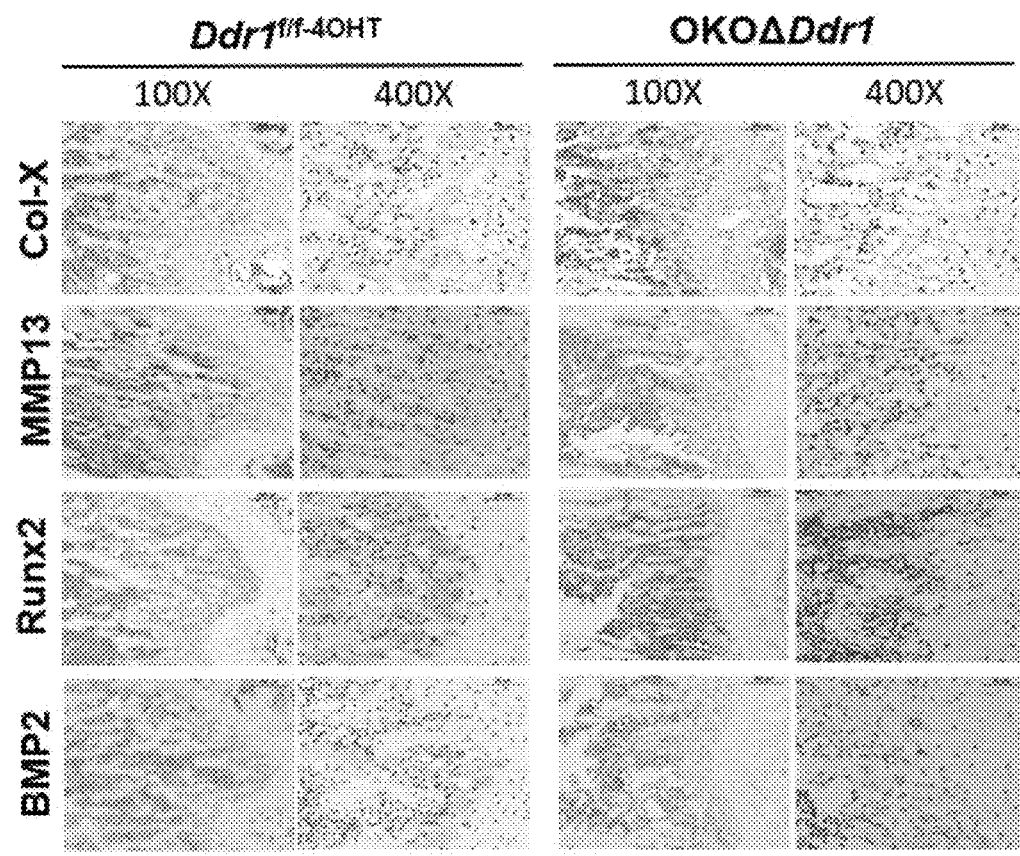
FIG. 8B shows IHC staining of Col-X, MMIP13, Runx2, and BMP2 in femurs from 4-week-old Ddr1$^{f/f-4OHT}$ and OKOΔDdr1 mice. Magnifications were 100× and 400× with scale bars of 200 μm and 50 μm, respectively.

To investigate whether Ddr1 knockout in osteoblasts influences chondrocyte function at the chondro-osseous interface, IHC stain for chondrocyte terminal differentiation markers, such as type X collagen (Col-X) and matrix metalloproteinase-13 (MMP13) was performed. The IHC results showed that knocking out Ddr1 in osteoblasts had no effect on either Col-X or MMP13 in the hypertrophic zone of the growth plate and the chondro-osseous interface (FIGS. 8B and 8C). Next, FIG. 8A shows that the gene expression of osteogenesis related markers, such as Runx2 and BMP2, was significantly lower in OKOΔDdr1 mice than in Ddr1$^{f/f\text{-}4OHT}$ mice. The Runx2 protein level was significantly decreased in 4-week-old OKOΔDdr1 mouse trabeculae (FIG. 8B). ALP is a hallmark of early development. In OKOΔDdr1 mice, the gene expression of ALP was decreased compared with that in Ddr1$^{f/f\text{-}4OHT}$ mice (FIG. 8A). In osteogenesis, CoM and OC are markers of late osteoblast differentiation. The gene expression of Col-I and OC was decreased by ~80% in OKOΔDdr1 mice (FIG. 8A). According to these results, the inventors demonstrated that osteoblasts with Ddr1 knockout delayed bone formation through downregulation of osteogenesis-related markers, indicating that Ddr1 in osteoblasts plays a critical role in regulating osteoblast activity during osteogenesis.

Three-point bending analysis was carried out for the 4-week-old Ddr1$^{f/f\text{-}4OHT}$ mice and OKOΔDdr1 mice to obtain the mechanical properties, including maximum load (expressed as "MaxLoad" in Table 1), break point, stiffness, area under the max curve (AUC1), area under the break curve (AUC2), ultimate stress, modulus, and toughness, in femur. The results in Table 1 (each group n≥6; * p≤0.05, ** p≤0.01. p value: compare with Ddr1$^{f/f\text{-}4OHT}$) shows a marked reduction in mechanical properties of the femur cortical bone of 4-week-old OKOΔDdr1 mice as compare with Ddr1$^{f/f\text{-}4OHT}$ mice, which proves that the knockout of Ddr1 in osteoblasts promotes changes in the internal mechanical structure of the femur and makes the femur have a higher risk of fractures.

TABLE 1

Mechanical properties in the femur

| Group | | Ddr1$_{f/f\text{-}4OHT}$ (Mean ± SE) | OKOΔDdr1 (Mean ± SE) | P value |
|---|---|---|---|---|
| MaxLoad | N | 10.68 ± 3.55 | 4.26 ± 0 | 0.001 ** |
| Break point | N | 8.31 ± 3.42 | 4.04 ± 0.01 | 0.01 * |
| stiffness(S) | N/mm$^2$ | 70.69 ± 31.13 | 33.5 ± 0.01 | 0.006 ** |
| AUC1 | J | 0.003 ± 0.0017 | 0.0012 ± 0.0099 | 0.01 * |
| AUC2 | J | 0.0059 ± 0.0031 | 0.0028 ± 0.0134 | 0.013 * |
| UStress | MPa | 0.53 ± 0.23 | 0.37 ± 0.19 | 0.188 |
| Modulus | GPa | 3.23 | 1.83 | 0.048 * |
| Toughness | MPa | 1.77 | 0.94 | 0.04 * |

Figure 9A:
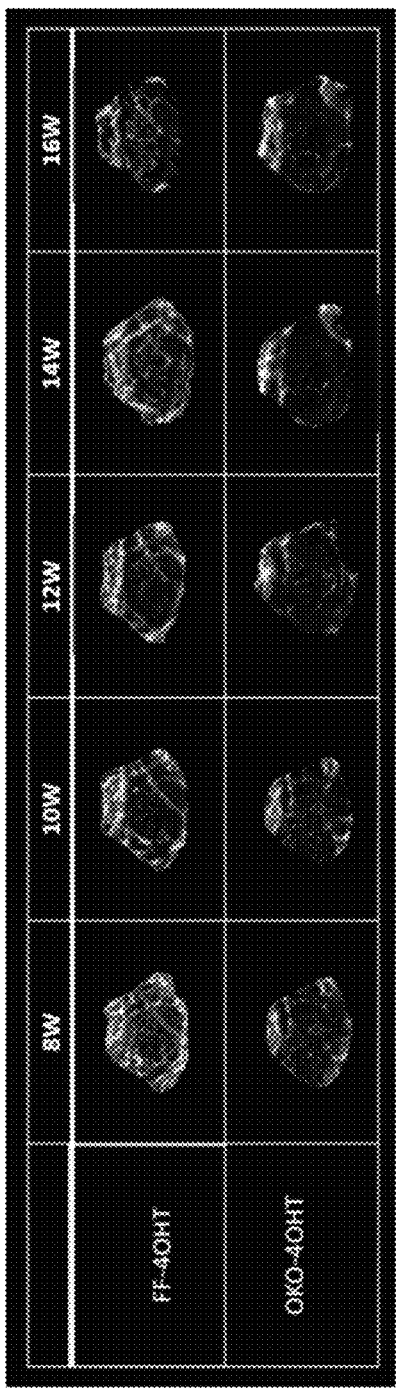
FIG. 9A shows micro-CT scanning results of the trabecular bone of femur in 8-week-old to 16-week-old OKO-4OHT mice and FF-4OHT mice.
Figure 9B:
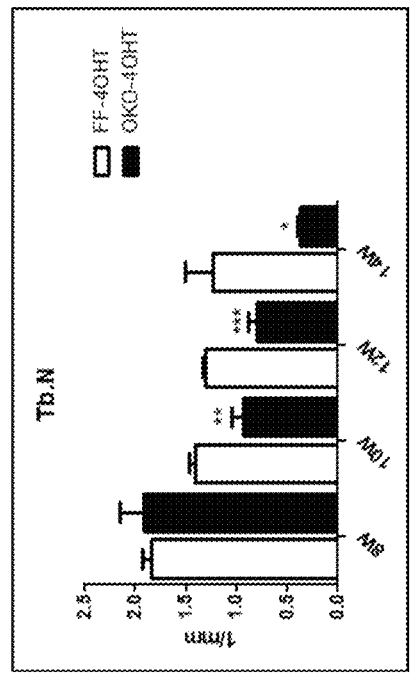
FIGS. 9B, 9C, 9D and 9E show (B) BV/TV, (C) Tb.N, (D) Tb.Th and (E) Tb. Sp of the trabecular bone of femur in 8-week-old to 16-week-old OKO-4OHT mice and FF-4OHT mice. Each group n=8.
Figure 9C:
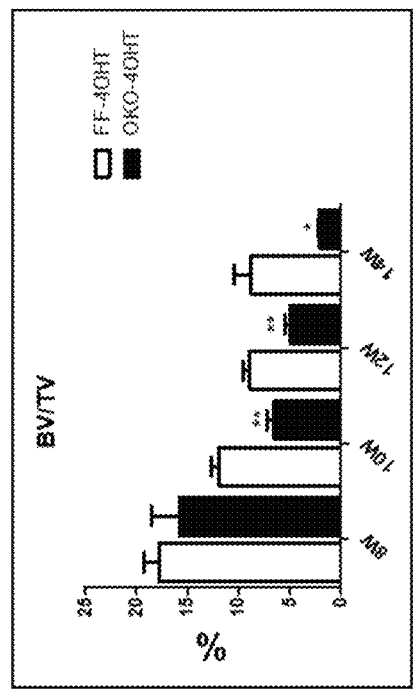
Figure 9D:
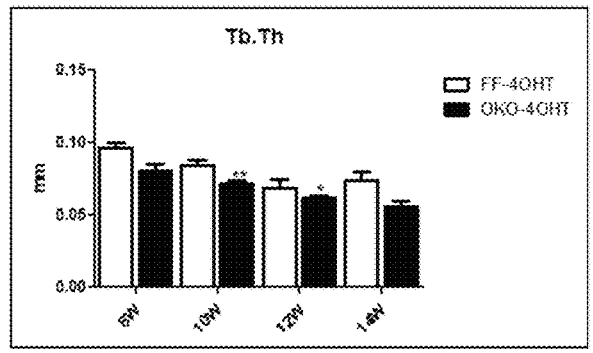
Figure 9E:
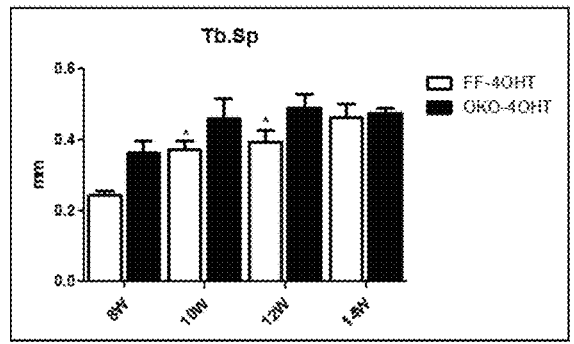
Figure 9F:
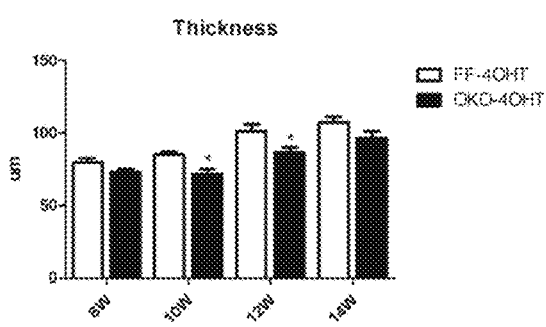
FIGS. 9F and 9G show (F) the cortical thickness and (G) cortical diameter in 8-week-old to 16-week-old OKO-4OHT mice and FF-4OHT mice. Each group n=6.
Figure 9G:
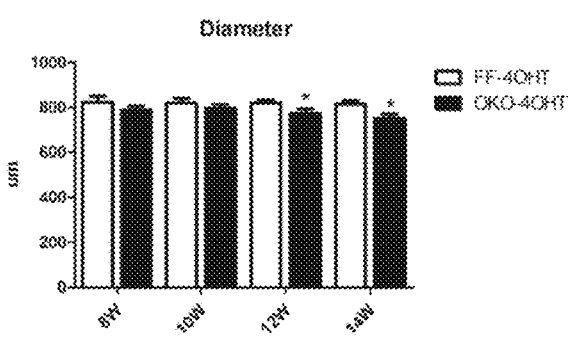

To investigate the effect of Ddr1 deletion in osteoblasts of mature mice, 7-week-old mature mice were injected with 4-OHT solution to activate Cre-Loxp system for deleting Ddr1 in osteoblasts. The three-dimensional micro-structures of the trabecular bone of femur of the OKO-4OHT mice and FF-4OHT mice (the control group) were analyzed by using high resolution micro-CT, and the results are shown in FIG. 9A. As shown in FIG. 9A, compared with the control group, FF-4OHT mice, the OKO-4OHT mice had obvious bone loss. Specifically, OKO-4OHT mice were induced a significant bone mass reduction in the trabecular bone of femur (approximately by 10%) at 16 week-old. As compared with FF-4OHT mice, the trabecular bone of femur of the OKO-4OHT mice showed a significant decrease of about 6% (p<0.0001, n=8) in the percentage of bone volume/total volume of the cortical bone (BV/TV, i.e., the bone volume density), the trabecular number (Tb.N) and the trabecular thickness (Tb.Th) and a significant increase (p<0.0001, n=8) in the trabecular spacing (Tb.Sp) (FIGS. 9B to 9E). Moreover, the cortical thickness (FIG. 9F) and cortical diameter (FIG. 9G) were also reduced in OKO-4OHT mice (approximately −8%) compared with FF-4OHT control mice (p<0.05, n=6). The increase in the cortical diameter is directly related to cortical bone formation. These data indicated that knockout Ddr1 in osteoblast exhibited a significant bone loss, which contributes to the osteopenia phenotype.

Figure 10A:
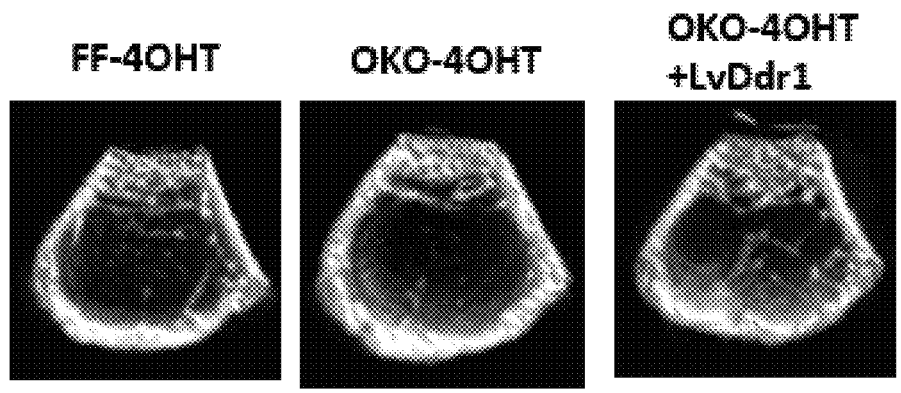
FIG. 10A shows micro-CT scanning results of the trabecular bone of femur in 14-week-old OKO-4OHT mice, FF-4OHT mice, and OKO-4OHT+LvDdr1 mice.
Figure 10B:
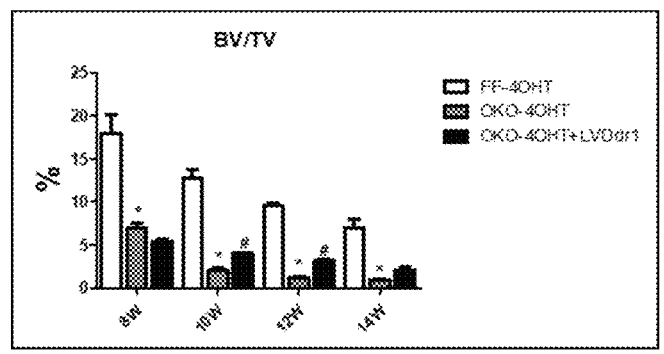
FIGS. 10B and 10C show (B) BV/TV and (C) Tb.N of the trabecular bone of femur in 8-week-old to 14-week-old OKO-4OHT mice, FF-4OHT mice, and OKO-4OHT+LvDdr1 mice.
Figure 10C:
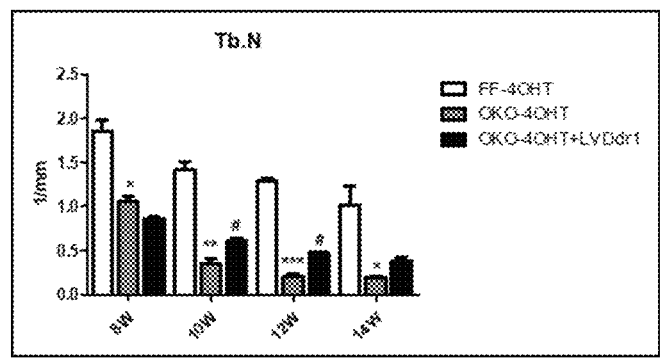

To confirm whether Ddr1 is a positive regulator in bone formation, lentivirus is used to overexpress Ddr1 in OKO-4OHT mice (which is obtained by injecting 4-OHT solution into 7-week-old mature mice for deleting Ddr1 in osteoblasts) by intra-femoral injection of lentivirus-expressing Ddr1 with $5*10^5$ transducing units/ml, and the resultant mice group is referred to as "OKO-4OHT+LvDdr1". The injection of lentivirus/vehicle was conducted once at 8 week-old in OKO-4OHT or FF-4OHT control mice. The results showed that the trabecular bone and cortical bone loss in femurs in OKO-4OHT+LvDdr1 mice was largely prevented by micro-CT scanning after being injected for 2 weeks (as shown in FIG. 10A). FIG. 10B shows that compared with the control group, i.e., FF-4OHT and OKO-4OHT mice, 10-week-old to 12-week-old OKO-4OHT+LvDdr1 mice can significantly relieve the bone loss caused by Ddr1 deletion. These results demonstrated that Ddr1 has the function in preventing bone loss.

3. The Increased Expression of Ddr1 can Treat or Alleviate Bone-Loss Related Diseases or Conditions Because bone metabolism is closely related to estrogen, mice with bilateral ovariectomy were used as a model for studying osteoporosis in postmenopausal animals.

Female mice were divided into a sham operation control group (Sham group) and 2 ovariectomized groups (Ovariectomy; OVX). The 2 ovariectomized groups include the vehicle group (OVX+Saline group) and the experimental group (OVX+LVDdr1 group). The mice group, OVX+LVDdr1 group, is obtained by intra-femoral injection of lentivirus-expressing Ddr1 with $5*10^5$ transducing units/mL during the ovariectomy operation.

Figure 11A:
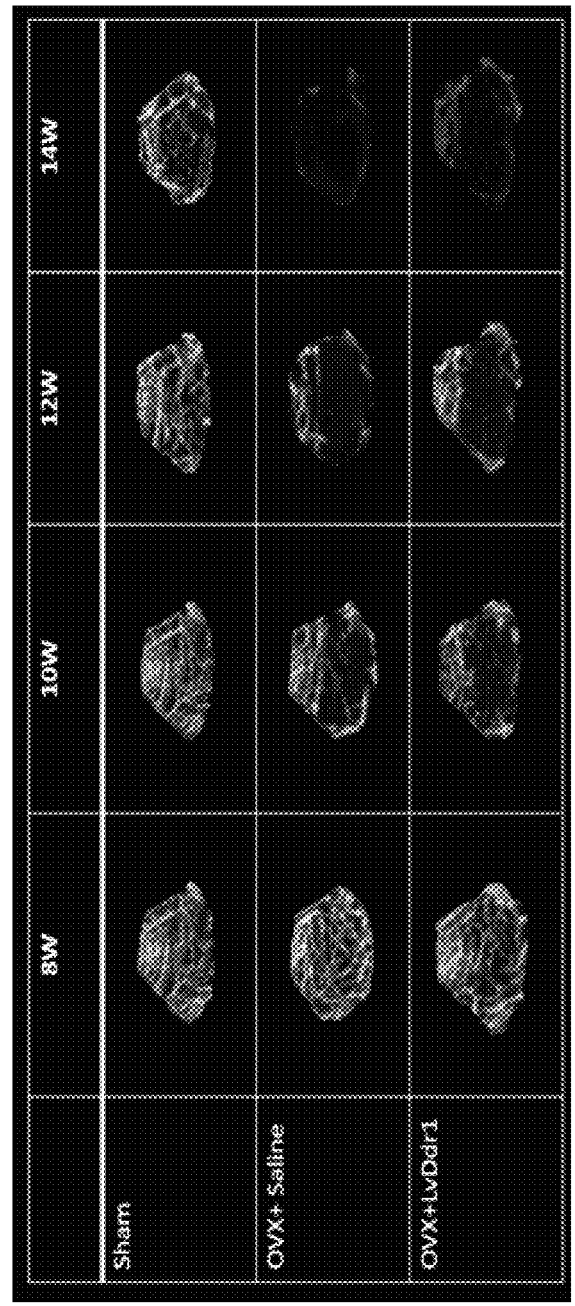
FIG. 11A shows micro-CT scanning results of the trabecular bone of femur in 8-week-old to 14-week-old mice in Sham group, OVX+Saline group, and OVX+LVDdr1 group.
Figure 11B:
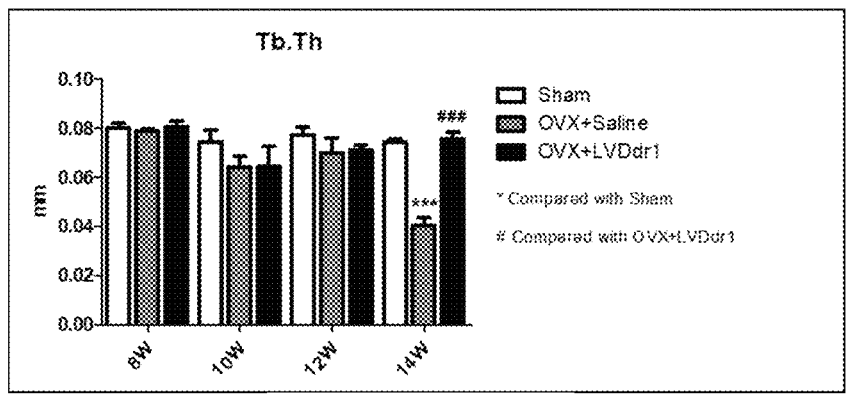
FIGS. 11B, 11C, 11D and 11E show (B) BV/TV, (C) Tb.Th, (D) Tb.N and (E) Tb.Sp of the trabecular bone of femur in 8-week-old to 14-week-old mice in Sham group, OVX+Saline group, and OVX+LVDdr1 group. N=3 in each group.
Figure 11C:
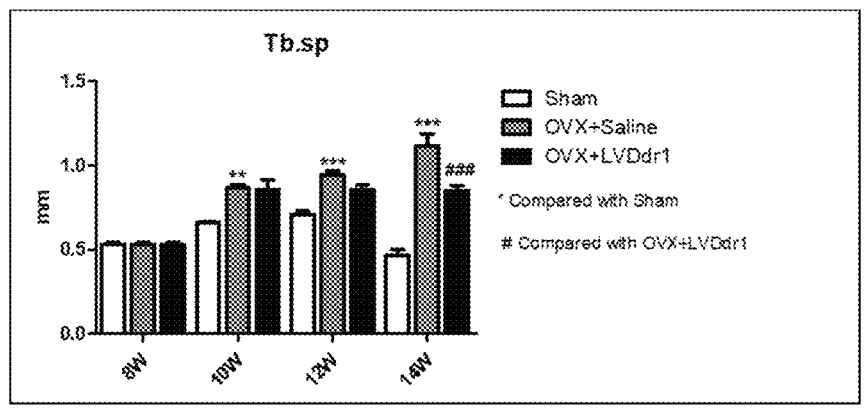
Figure 11D:
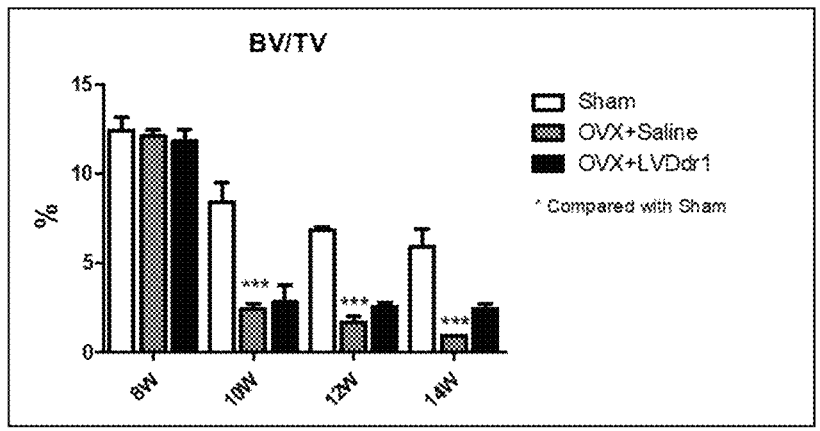
Figure 11E:
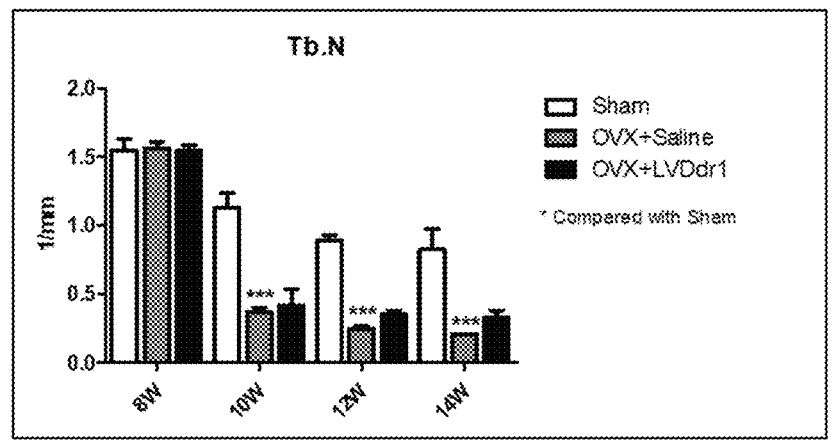
Figure 11F:
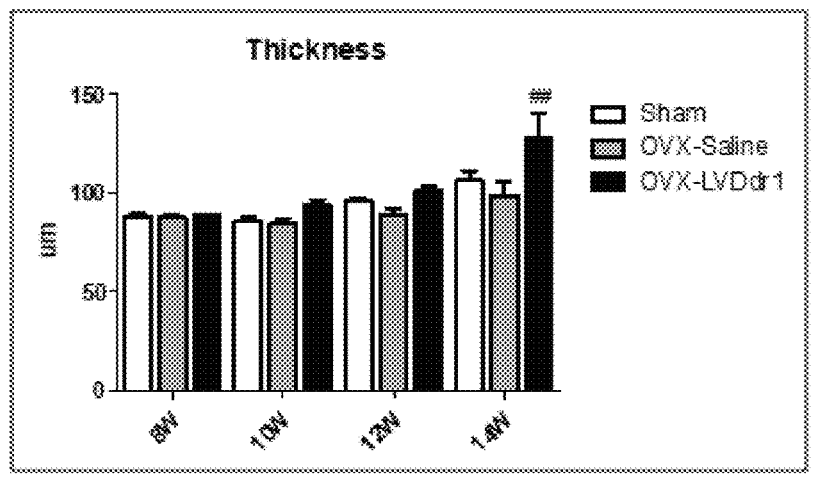
FIGS. 11F and 11G show (F) the cortical thickness and (G) cortical diameter in 8-week-old to 14-week-old mice in Sham group, OVX+Saline group, and OVX+LVDdr1 group. N=3 in each group.
Figure 11G:
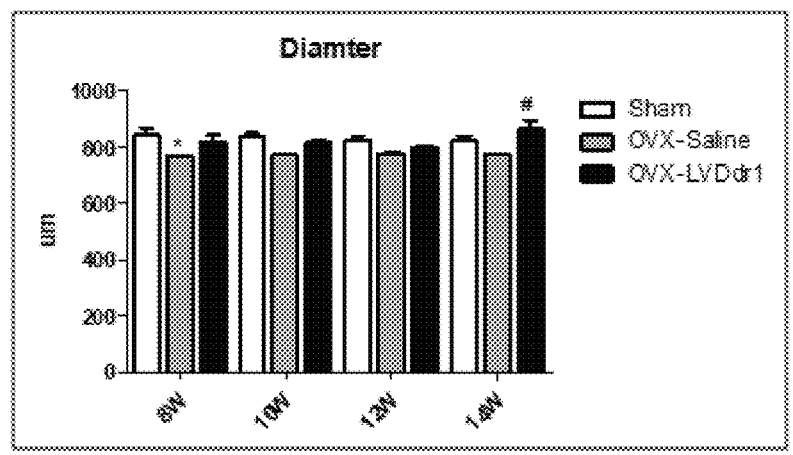

As compared with the mice in the control group (sham group), it is confirmed that the mice in the OVX+Saline group had significant bone loss and thus the OVX mouse model is successful (as shown in FIG. 11A), and bone loss in the OVX+LVDdr1 group, in which the Ddr1 protein level is overexpressed in osbleasts, is slower. It can be seen in FIGS. 11B to 11E that in 8-week-old to 14-week-old mice of OVX+LVDdr1 group, the thickness of the trabecular bone (Tb.Th) and the trabecular spacing (Tb.Sp) are significantly recovered (p<0.0001) as compared with the sham group, which means that osteoporosis can be effectively treated by the increased Ddr1 level. Moreover, in 8-week-old to 14-week-old mice of OVX+LVDdr1 group, the cortical bone has significant increase in thickness (FIG. 11F, p<0.0001, n=3) and diameter (FIG. 11G, p<0.05, n=3) as compared with the control group. The results of the above experiments confirms that the increased expression of Ddr1 can indeed slow down bone loss and thus treat or alleviate bone-loss related diseases or conditions, such as osteoporosis.

The present invention provides a method or a composition for treating or alleviating a bone-loss related disease or condition in a subject. The method comprises a step of administering to the subject an effective amount of the composition that increases a level of DDR1 protein in the subject for treating or alleviating the bone-loss related disease or condition in the subject. In some embodiments, the subject is a human and is diagnosed with the bone-loss related disease. In some embodiments, the human is female, particularly a post-menopausal female. In some embodiments, the human has decreased ovarian function or ovarian failure. In some embodiments, the bone-loss related disease or condition is primary osteoporosis, secondary osteoporosis, osteogenesis imperfecta, osteodystrophy, osteopenia, Paget's disease, osteolytic lesions produced by bone metastasis, radiotherapy, or chemotherapy, periodontal disease, alveolar bone loss, bone loss due to sex hormone deficiency, bone loss due to metastatic cancer, bone loss caused by an inflammatory disease, osteotomy bone loss, childhood idiopathic bone loss, curvature of the spine, or bone fractures. In some embodiments, the bone-loss related disease or condition is osteoporosis, and the osteoporosis may be osteoporosis caused by aging, postmenopausal primary osteoporosis, or osteoporosis caused by ovariectomy.

The composition that treat or alleviate the bone-loss related disease or condition by increasing a level of DDR1 protein in the subject can be achieved by any manner that can be used to increase a protein level in the subject. Some examples of such compositions are described below, but manners that can be used to increase a protein level in a subject are not limited to the examples listed.

In some embodiments, the composition may be a small molecule drug, a peptide drug, or a protein drug. The composition may comprises a polynucleotide encoding a human DDR1 protein or a small molecule protein of DDR1. The polynucleotide or small molecule may be carried by a vehicle, which may be nanoparticle, microsome, lysosome or the like.

In some embodiments, virally based system is used for gene transfer into mammalian cells. For example, retroviruses (such as adenovirus and lentivirus) provide a convenient platform for gene delivery systems. In some embodiments, DDR1 gene is inserted into a vector and packaged into retroviral particles using known techniques. The recombinant virus is then isolated and delivered to cells (such osteoblast cells) of the subject either in vivo or ex vivo.

In some embodiments, the composition comprises a gene therapy vector, and the gene therapy vector includes a nucleic acid sequence connected with an osteoblast specific promoter and encoding a DDR1 protein. The vector provided herein includes any suitable gene expression vector that is capable of being delivered to a tissue of interest (such as bone) and which will provide for the expression of the gene of DDR1 in the selected tissue of interest. In some embodiments, the gene therapy vector is transfected into osteoblasts ex vivo, and then the osteoblasts containing the therapy vector is injected into bones (such as leg bones) or joints (such as hip joints or knee joints) of the subject.

Provided herein are gene therapy vectors in which a nucleic acid, such as a DNA, encoding DDR1 protein, optionally having a signal peptide. The gene therapy vector optionally comprises an internal ribosomal entry sequence. Vectors derived from retroviruses such as the lentivirus are suitable tools to achieve long-term gene transfer since they allow long-term, stable integration of a transgene and its propagation in daughter cells. Lentiviral viral vectors have the added advantage over vectors derived from onco-retroviruses such as murine leukemia viruses in that they are capable of transducing non-proliferating cells, such as hepatocytes and neurons. They also have the added advantage of low immunogenicity.

As above, comparing to the prior art, the present invention can reduce the symptoms and the risk of complications of menopausal women, increase bone mineral content, bone density and bio-mechanical strength of bone, and slow down osteoporosis through administering to a subject in need of such treatment a composition.

If necessary, the above compositions can be formulated into tablets, powders, granules, capsules, microlipid capsules, injections, solvents, drops and freeze drying agents by adding excipients, isotonic agents, stabilizers, preservatives, analgesics, or the like. These can be formulated by well known methods.

The above composition can be directly used in a patient's diseased site, or injected into a joint or a bone to reach the diseased site. In some embodiments, the composition is a pharmaceutical composition and is optionally mixed with a pharmaceutically acceptable adjuvant or carrier. The pharmaceutical composition may additionally comprise other pharmaceutically active agents, such as a known drug for treating bone loss. In some embodiments, the pharmaceutical composition is formulated for administration: by inhalation, intraperitoneal, intravenous, intramuscular, subcutaneous, intracranial, intraventricular, oral, enteral, parenteral, intranasal, dermal, subcutaneous, topical, sublingual or transbuccal manner, or via catheter, via a lavage, via continuous infusion, via infusion, via inhalation, via injection, via local delivery, or via localized perfusion. In some embodiments, the pharmaceutical composition is formulated as a unit dose.

The pharmaceutical composition in the present invention is in the form of a suitable preparation unit, which may be an oral solid preparation or an injection preparation. The oral solid preparation may be any one of a tablet, a capsule, a pill, and a granule. The administration preparation for injection can be any one of a water injection, a powder injection, and an infusion. The form of the preparation unit of the present invention is preferably an injection preparation, more preferably a small volume parenteral for injection or a powder injection.

In an embodiment, the pharmaceutical composition above can be administered alone or together with other agents, and the regime is performed according to the pharmaceutically routine method.

In an embodiment, the pharmaceutical composition above comprises a pharmaceutically acceptable carrier or medium, such as an excipient, a stabilizer, a solubilizer, an emulsifier, a suspending agent, a buffer, an isotonic agent, an antioxidant or a preservative, and the like. The following examples are given, but the present invention is not limited thereto, and a carrier or medium known in the art may be used. An excipient such as starch or lactose that does not have a pharmacological effect itself is preferable. The stabilizing agent comprises albumin, gelatin, sorbitol, mannitol, lactose, sucrose, trehalose, maltose, glucose, etc., preferably sucrose or trehalose. The solubilizer contains ethanol, glycerin, propylene glycol, polyethylene glycol, and the like. The emulsifier comprises lecithin, aluminum stearate or sorbitan sesquioleate. The suspending agent comprises polyethylene glycol, polyvinylpyrrolidone (PVP) or carboxymethylcellulose (CMC). The isotonic agents include sodium chloride, glucose, and the like. The buffer contains citrate, acetate, boric acid or phosphate. The antioxidant contains ascorbic acid, sodium hydrogen sulfite, sodium metabisulfite, and the like. The preservative contains phenol or the like.

The pharmaceutical composition in the present invention is preferably a targeting pharmaceutical composition, which may be delivered to a target cell, a target tissue or an organ at increased proportions relative to the blood circulation, lymphoid system, and other cells, tissues or organs. When this is achieved, the therapeutic effects of the targeting pharmaceutical composition is increased, while the scope and severity of the side effects and toxicity is decreased. When the drug is delivered in the form of a targeting pharmaceutical composition, the dosage at which the therapeutic effect can be achieved may be lower than that of the non-targeting pharmaceutical composition. Therefore, the medicament or pharmaceutical composition for treatment can be administered at a lower dose without detracting from its effectiveness, but at the same time reducing its side effects and toxicity.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for treating or alleviating an osteoporosis in a subject, comprising:
   identifying the subject having the osteoporosis; and
   administering to the subject an effective amount of a composition that increases a level of Discoidin Domain Receptor 1 (DDR1) protein in bone or joints in the subject, wherein the composition comprises a nucleic acid encoding the DDR1 protein.

2. The method as claimed in claim 1, wherein the subject is human.

3. The method as claimed in claim 2, wherein the human is female.

4. The method as claimed in claim 1, wherein the subject is a post-menopausal female.

5. The method as claimed in claim 4, wherein the subject has decreased ovarian function or ovarian failure.

6. The method as claimed in claim 1, wherein the osteoporosis is a primary osteoporosis or a secondary osteoporosis.

7. The method as claimed in claim 1, wherein the composition comprises a cell comprising the nucleic acid encoding the DDR1 protein.

8. The method as claimed in claim 1, wherein the composition comprises a vector including the nucleic acid encoding the DDR1 protein.

9. The method as claimed in claim 8, wherein the vector is a lentivirus vector.

10. The method as claimed in claim 8, wherein administering the composition comprises injecting the composition into bone or joints.

11. The method as claimed in claim 1, wherein the composition includes a vector that is a non-viral vector.

12. The method as claimed in claim 11, wherein the non-viral vector includes a liposome-mediated delivery vector or a microsome-mediated delivery vector.

13. A method for treating or alleviating a bone-loss-related disease or condition in a subject, comprising:
    administering to the subject an effective amount of a composition that increases a level of Discoidin Domain Receptor 1 (DDR1) protein in bone or joints in the subject for treating or alleviating the bone-loss-related disease or condition in the subject, wherein the composition comprises a nucleic acid encoding the DDR1 protein.

14. The method as claimed in claim 13, wherein the subject is a human and is diagnosed with the bone-loss-related disease.

15. The method as claimed in claim 13, wherein the bone-loss-related disease or condition is primary osteoporosis, secondary osteoporosis, osteogenesis imperfecta, osteodystrophy, osteopenia, Paget's disease, osteolytic lesions produced by bone metastasis, radiotherapy, or chemotherapy, periodontal disease, alveolar bone loss, bone loss due to sex hormone deficiency, bone loss due to metastatic cancer, bone loss caused by an inflammatory disease, osteotomy bone loss, childhood idiopathic bone loss, curvature of the spine, or bone fractures.

16. The method as claimed in claim 13, wherein the composition specifically or preferentially increases the level of DDR1 protein.

* * * * *